(12) United States Patent
Stein

(10) Patent No.: US 11,869,656 B1
(45) Date of Patent: Jan. 9, 2024

(54) PROVIDER ASSESSMENT SYSTEM, METHODS FOR ASSESSING PROVIDER PERFORMANCE, METHODS FOR CURATING PROVIDER NETWORKS BASED ON PROVIDER PERFORMANCE, AND METHODS FOR DEFINING A PROVIDER NETWORK BASED ON PROVIDER PERFORMANCE

(71) Applicant: Embold Health, Inc., Nashville, TN (US)

(72) Inventor: Daniel Stein, Fayetteville, AR (US)

(73) Assignee: Embold Health, Inc., Nashville, TN (US)

( * ) Notice: Subject to any disclaimer, the term of this patent is extended or adjusted under 35 U.S.C. 154(b) by 324 days.

(21) Appl. No.: 16/547,983

(22) Filed: Aug. 22, 2019

Related U.S. Application Data

(60) Provisional application No. 62/722,034, filed on Aug. 23, 2018, provisional application No. 62/722,036, filed on Aug. 23, 2018, provisional application No. 62/722,026, filed on Aug. 23, 2018.

(51) Int. Cl.
| | |
|---|---|
| *G06Q 10/00* | (2023.01) |
| *G06Q 10/06* | (2023.01) |
| *G16H 40/20* | (2018.01) |
| *G16H 15/00* | (2018.01) |
| *G16H 10/60* | (2018.01) |

(52) U.S. Cl.
CPC ............ *G16H 40/20* (2018.01); *G16H 10/60* (2018.01); *G16H 15/00* (2018.01)

(58) Field of Classification Search
CPC ........ G06N 5/025; G16H 10/60; G16H 15/00; G16H 30/40; G16H 50/20; G16H 50/30; G16H 50/70; G16H 10/40; G16H 20/40; G16H 40/67; G16H 50/50
See application file for complete search history.

(56) References Cited

U.S. PATENT DOCUMENTS

| | | |
|---|---|---|
| 9,710,600 B1 | 7/2017 | Dunleavy et al. |
| 2006/0100904 A1 | 5/2006 | Jee et al. |
| 2009/0125348 A1 | 5/2009 | Rastogi |
| 2011/0077958 A1* | 3/2011 | Breitenstein ........... G06Q 10/10 705/2 |
| 2013/0117033 A1 | 5/2013 | Mohlenbrock |

(Continued)

*Primary Examiner* — Maroun P Kanaan
(74) *Attorney, Agent, or Firm* — TraskBritt

(57) ABSTRACT

Methods of assessing a performance of a provider include receiving, from a third-party system, claims data, applying one or more defined performance measures to the claims data to determine measure scores of one or more providers, the measure scores being related to key-clinical decision points within condition-based patient journeys represented in the claims data, outputting one or more data packages representing the determined measure scores, applying a principal components analysis to the one or more data packages to determine composite performance scores of the one or more providers based on the determined measure scores, wherein the determined composite performances scores are provider specific, generating a performance data package including the determined composite performance scores, and causing the determined composite performance scores to be displayed within a graphical user interface of an application of a client device.

21 Claims, 22 Drawing Sheets

(56) References Cited

U.S. PATENT DOCUMENTS

| | | |
|---|---|---|
| 2013/0238353 A1 | 9/2013 | Hennenfent |
| 2014/0122100 A1 | 5/2014 | Fillmore |
| 2015/0100336 A1* | 4/2015 | Ford ................. G06Q 30/0201 705/2 |
| 2016/0196407 A1 | 7/2016 | Caballero et al. |
| 2019/0087765 A1 | 3/2019 | Brown et al. |
| 2019/0095874 A1* | 3/2019 | Bellrose ............... G06Q 30/018 |

* cited by examiner

LOW-RISK OBSTETRICS

APPROPRIATENESS
- Prenatal fetal ultrasound rates
- Elective induction without medical indication
- C-section rate
- Episiotomy, Forceps, Vacuum delivery

QUALITY
- Receipt of prenatal screening
- Post-delivery complications
  - ICU admission
  - Transfusion
  - Infection
  - DVT/PE
  - Uterine rupture
  - Perineal laceration
  - Unanticipated operation
  - Re-admission
  - Unplanned ED visit

COST
- Prenatal fetal ultrasound rates
- Elective induction without medical indication
- C-section rate
- Episiotomy, Forceps, Vacuum delivery

*FIG. 3A*

JOINT CARE - ORTHOPEDIC SURGERY

APPROPRIATENESS
- Arthroscopy for newly diagnosed osteoarthritis (OA)
- Knee/hip arthroplasty within 1y of OA diagnosis
- Use of physical therapy prior to knee/hip arthroplasty
- Preoperative stress testing
- Use of institutional post-acute care
- Use of preoperative MRI patients undergoing knee/hip arthroplasty

QUALITY
- Pre-operative joint injection utilization
- Post-operative complications
  - ICU admission
  - Transfusion
  - Infection
  - DVT/PE
  - Mechanical complications
- Unplanned ED visit rate
- Postoperative re-admission rate
- Joint hardware removal rate

COST
- Total costs of care for newly diagnosed knee/hip pain over 1-year

*FIG. 3B*

SPINE CARE - ORTHOPEDIC SURGERY, NEUROSURGERY

| APPROPRIATENESS | QUALITY | COST |
|---|---|---|
| • Early surgery for newly-diagnosed back pain<br>• Rate of spinal fusion<br>• Rate of anterior/posterior spinal fusion<br>• Rate of fusion for spondylolisthesis<br>• Use of physical therapy prior to spine surgery<br>• Use of injections prior to spine surgery | • Postoperative complications<br>  • ICU admission<br>  • Transfusion<br>  • Infection<br>  • DVT/PE<br>  • Mechanical complications<br>• Rate of hardware removal within one-year of index procedure<br>• Use of institutional post-acute care<br>• Rate of secondary spine surgery | • Total costs of care for newly diagnosed lumbar back pain over 1-year |

*FIG. 3C*

CARDIOLOGY

| APPROPRIATENESS | QUALITY | COST |
|---|---|---|
| • Use of stress testing among patients with stable CAD<br>• Use of PCI among patients with stable CAD<br>• ICU utilization after elective PCI | • Monitoring of CAD patients on ACE/ARB<br>• Adherence to DM medications among patients with CAD and DM<br>• Adherence to statin therapy among patients with CAD<br>• Adherence to beta blocker therapy among patients with CAD and HTN or DM<br>• Complication rate after elective PCU | • Total costs of care for CAD over 1-year |

*FIG. 3D*

PRIMARY CARE

APPROPRIATENESS
- Use of PSA testing in men over 75y
- Cervical cancer screening for women over 65 years
- Use of unnecessary preoperative testing
  - Pulmonary function
  - Stress testing
  - Imaging
- Use of CT sinuses for uncomplicated sinusitis
- Use of imaging for uncomplicated low back pain

QUALITY
- Rate of retinal exam for adults with DM
- Asthma controller medication ratio
- Avoidance of antimicrobial therapy among adults with bronchitis
- Rates of guideline-adherent cancer screening
- Osteoporosis management among women with fracture
- Referral intensity

COST
- Risk-adjusted annual per member per month health care spend

*FIG. 3E*

GASTROENTEROLOGY

APPROPRIATENESS
- Colonoscopy interval among adults with history of adenomatous polyps
- Screening colonoscopy adenoma detection rate
- Repeat screening colonoscopy within 1 yr
- Number of IBD patient-days on steroids
- Use of upper endoscopy after diagnosis of GERD
- Upper endoscopy interval among adults with Barrett's esophagus

QUALITY
- Proportion of IBD patients on biologics
- Screening for hepatocellular carcinoma in patients with cirrhosis
- Rates of antiviral use among patients with chronic hepatitis C
- Hospital visit rate after colonoscopy
- Hospital visit rate after upper endoscopy
- Hospital visit rate among adults with IBD

COST
- Total costs of care for newly diagnosed GERD over 1-year
- Total costs of care for newly diagnosed IBD over 1-year

*FIG. 3F*

PULMONOLOGY

APPROPRIATENESS
- Use of sleep studies among patients with chronic fatigue/insomnia
- Use of CT surveillance for pulmonary nodule longer than recommended interval
- Use of bronchoscopy for pneumonia diagnosis
- Lung cancer diagnosis rate after diagnostic bronchoscopy

QUALITY
- Spirometry rate among patients with newly diagnosed COPD
- Admission rate among patients with COPD
- Asthma medication ratio
- Admission rate among patients with asthma
- COPD on appropriate medication regimen
- Use of burst steroids among patients with COPD

COST
- Total costs of care for newly diagnosed COPD over 1-year
- Total costs of care for newly diagnosed asthma over 1-year

*FIG. 3G*

PROVIDER ASSESSMENT SYSTEM, METHODS FOR ASSESSING PROVIDER PERFORMANCE, METHODS FOR CURATING PROVIDER NETWORKS BASED ON PROVIDER PERFORMANCE, AND METHODS FOR DEFINING A PROVIDER NETWORK BASED ON PROVIDER PERFORMANCE

CROSS-REFERENCE TO RELATED APPLICATIONS

This application claims the benefit under 35 U.S.C. § 119(e) of U.S. Provisional Patent Application Ser. No. 62/722,036, filed Aug. 23, 2018, U.S. Provisional Patent Application Ser. No. 62/722,034, filed Aug. 23, 2018, and U.S. Provisional Patent Application Ser. No. 62/722,026, filed Aug. 23, 2018, the disclosures of which are hereby incorporated herein in their entireties by this reference.

TECHNICAL FIELD

This disclosure relates generally to a provider assessment system for assessing provider performance based on performance measures applied to claims data. This disclosure further relates to curating provider networks based on performance scores of providers within the provider network. This disclosure also related to modifying and optimizing provider networks based on the performances scores of the provider within the provider networks.

BACKGROUND

Theoretically, services that healthcare providers (e.g., medical doctors, dentists, physician's assistants, nurse practitioners, etc.) deliver to treat a group of patients with the same medical condition should fall within a tight range. Observed variation should generally be attributable to individual and population differences, for example, due to complications that arise from lifestyle (e.g., overweight, smoking), due to inter-related health conditions and/or due to socioeconomics and geography. However, for a given medical condition, there are a subset of providers (some estimates put it at 20-40% of providers that provide services in each practice area) that deliver significantly more services (i.e., care) than other providers. While sometimes these services are necessary, often the services are unnecessary, adding excess costs for patients, payers, and employers. Moreover, studies have shown that unnecessary medical care, especially unnecessary surgical care, may lead to downstream complications requiring additional evaluation and management.

Payers, third-party administrators, health maintenance organizations, and government agencies employ significant technical and policy resources to optimize the delivery of healthcare services and to identify these inefficient providers. For example, one common policy technique is to bundle payments for healthcare services associated with the treatment of a medical condition or performing a procedure. An episode of care generally refers to the horizon over which a, for example, bundled payment applies.

Generally, claims data serve as the cornerstone of analysis of episodes of care due to the widespread availability of billing data in the context of the richness of resource utilization and clinical information contained in claims data. Defining episodes of care appropriately is critical for bundled payment models to improve efficiency while still permitting providers to deliver high quality healthcare services. If episodes of care are defined too narrowly, errant assumptions are often made surrounding the clinical necessity of health care services rendered. If episodes of care are defined too broadly, there may be unintended heterogeneity in services delivered calling into question the validity of between-episode comparisons. Claims are derived from the billing process associated with health care delivery, wherein a provider delivers a service to an individual patient and submits an electronic claim to the payer which, after inspection and correction, is transmitted to the payer. The claim is subsequently adjudicated by the payer and, ultimately, payment is rendered for the services provided. Electronic claims typically include fields and data for services (including codes according to predetermined coding conventions and information added by a provider), dates, prices, provider and group identifiers, and more. The problems with episodic care models appear to be inherent in the concept of episodic care, as such the inventors of the present disclosure appreciate a need for a new manner to track patient journeys.

BRIEF SUMMARY

The various embodiments described below provide benefits and/or solve one or more of the foregoing or other problems in the art with systems and methods for assessing provider performance and defining patient journeys. Some embodiments of the present disclosure include a method of generating a performance measure, comprising: first mapping at least one clinical priority area and at least one candidate measure concept to one or more coding fields of claims data; defining at least one first performance measure based on the one or more coding fields of claims data mapped to the at least one clinical priority area and the at least one candidate measure concept; performing one or more validation processes; obtaining a validation result responsive to the one or more validation processes; and second mapping the at least one clinical priority area and the at least one candidate measure concept to one or more coding fields of claims data responsive to the validation result obtaining at least one final performance measure responsive the second mapping.

Some embodiments of the present disclosure include system comprising: at least one processor; and at least one non-transitory computer-readable storage medium storing instructions thereon that, when executed by the at least one processor, cause the system to: upon obtaining at least one clinical priority area and at least one candidate measure concept, first map the at least one clinical priority area and the at least one candidate measure concept to one or more coding fields of claims data; define at least one first performance measure based on the one or more mapped coding fields of claims data; validate the at least one first performance measure via at least one of an internal validation process and an external validation process; second map the at least one clinical priority area and the at least one candidate measure concept to one or more coding fields of claims data based on an obtained validation result; and obtaining at least one final performance measure responsive to the second mapping.

One or more embodiments of the present disclosure include a method of determining a performance score of a provider, comprising: first mapping at least one clinical priority area and at least one candidate measure concept to one or more coding fields of claims data; defining at least one first performance measure based on the one or more coding fields of claims data mapped to the at least one clinical priority area and the at least one candidate measure concept; performing one or more validation processes; obtaining a validation result responsive to the one or more validation processes; second mapping the at least one clinical priority area and the at least one candidate measure concept to one or more coding fields of claims data responsive to the validation result; obtaining at least one final performance measure responsive the second mapping; obtaining, from a third-party, claims data include data specific to the provider; and applying the at least one final performance measure to the claims data to determine at least one composite performance score of the provider.

BRIEF DESCRIPTION OF THE DRAWINGS

Various embodiments will be described and explained with additional specificity and detail through the use of the accompanying drawings in which:

FIGS. 3A-3G depict performance measures within given domains (e.g., appropriateness, effectiveness, and/or cost) that a provider assessment system can utilize to measure provider performance in accordance with one or more embodiments;

DETAILED DESCRIPTION

Figure 1:
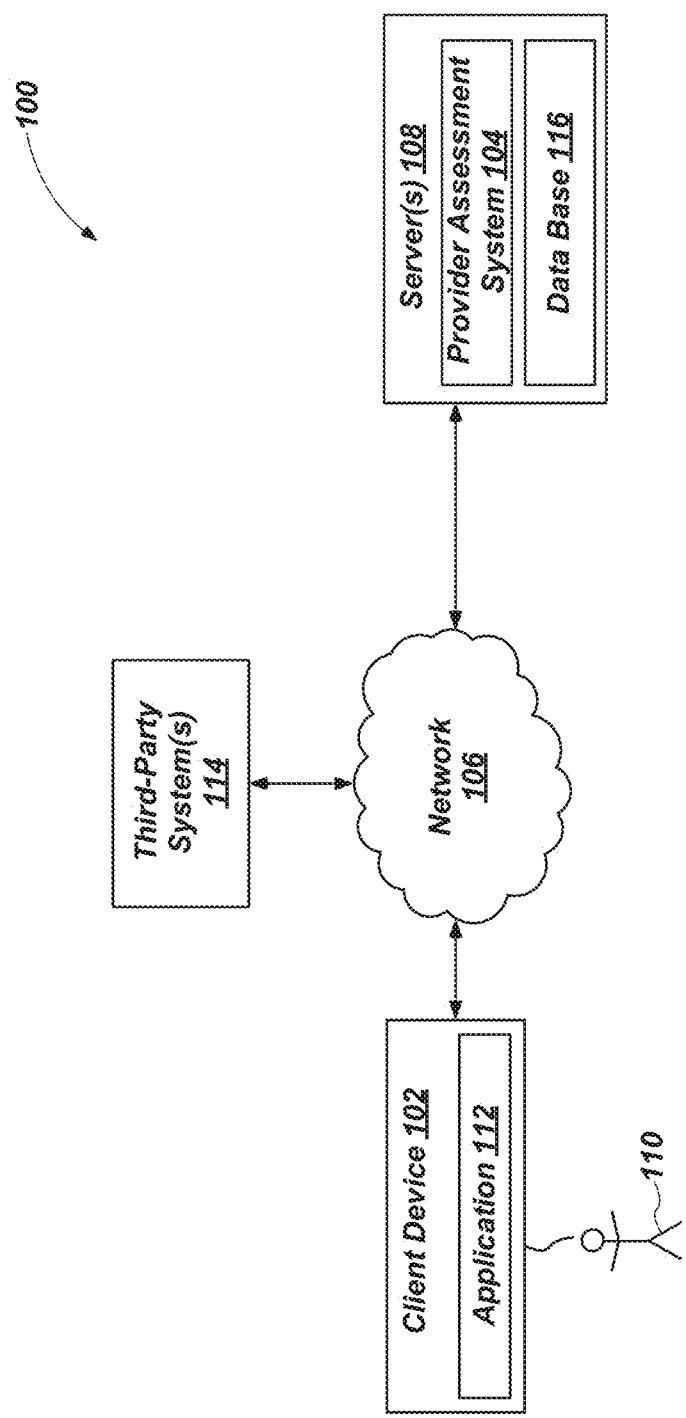
FIG. 1 illustrates a schematic representation of an environment within which a provider assessment system can operate in accordance with one or more embodiments of the present disclosure.

The illustrations presented herein are not actual views of any particular provider assessment system, or any component thereof, but are merely idealized representations, which are employed to describe the present invention.

As used herein, the singular forms following "a," "an," and "the" are intended to include the plural forms as well, unless the context clearly indicates otherwise.

As used herein, the term "may" with respect to a material, structure, feature, function, or method act indicates that such is contemplated for use in implementation of an embodiment of the disclosure, and such term is used in preference to the more restrictive term "is" so as to avoid any implication that other compatible materials, structures, features, functions, and methods usable in combination therewith should or must be excluded.

As used herein, any relational term, such as "first," "second," etc., is used for clarity and convenience in understanding the disclosure and accompanying drawings, and does not connote or depend on any specific preference or order, except where the context clearly indicates otherwise.

As used herein, the term "substantially" in reference to a given parameter, property, act, or condition means and includes to a degree that one skilled in the art would understand that the given parameter, property, or condition is met with a small degree of variance, such as within acceptable manufacturing tolerances. By way of example, depending on the particular parameter, property, or condition that is substantially met, the parameter, property, or condition may be at least 90.0% met, at least 95.0% met, at least 99.0% met, or even at least 99.9% met.

As used herein, the term "about" used in reference to a given parameter is inclusive of the stated value and has the meaning dictated by the context (e.g., it includes the degree of error associated with measure of the given parameter, as well as variations resulting from manufacturing tolerances, etc.).

As used herein, the term "provider" refers generally to a health care provider including any conventional health care provider (e.g., general practitioners (e.g., internal medicine, family practice, emergency room, general surgery doctors, etc.) and/or specialty doctors (e.g., cardiologists, pediatric doctors, obstetricians and gynecologists, optometrists, ophthalmologists, orthopedic surgeons, etc.)). The term "provider" also includes physician assistants, nurse practitioners, and other healthcare providers that typically enjoy independent practice rights.

As used herein, the term "domain" may refer to categories of performance scores. For instance, the term "domain" may refer to the categories of appropriateness, effectiveness, and/or cost as performance scores.

As used herein, a provider "specialty" may refer to a practice area of a provider such as, e.g., cardiology, pediatrics, gynecology, optometry, ophthalmology, orthopedic surgery, obstetrics, etc.

One or more embodiments of the present disclosure include a provider assessment system for determining performance scores of providers based on defined performance measures. For instance, a provider assessment system may determine performance scores such as an appropriateness score, an effectiveness score, and/or a cost score. In particular, the system of the present disclosure applies rigorous scientific evaluation to objectively identify health care providers delivering necessary, high-quality, and/or cost-effective care. As such the system of the present disclosure empowers employers, health plans, and health systems to identify top performing providers, top performing care settings, and/or top performing provider-setting pairs.

As non-limiting examples, the appropriateness score may reflect whether or not a given provider delivers care only when the care is necessary, the effectiveness score may reflect how well the given provider's delivered care achieves an appropriate (e.g., a correct and/or desirable) patient outcome, and the cost score may reflect whether the given provider delivers care efficiently at a reasonable cost relative to the provider's peers. In some embodiments, a provider assessment system may generate the composite performance scores at the domain (e.g., appropriateness, effectiveness, and/or cost) level and/or at an overall level (e.g., a compilation of domains and by physician, physician group, and/or a health system (e.g., a hospital or group of hospitals)).

In one or more embodiments, a provider assessment system may predict performance scores of providers given a key-clinical decision point in a patient journey. For instance, a provider assessment system may predict that actions (e.g., behavior) of a provider for a next key-clinical decision point. In some embodiments, a provider assessment system may fit a predictive model to data representing past performance in order to predict future provider behavior. As a non-limiting example, a provider assessment system 104 may analyze and/or process the past performance data via fixed effects models, random effects models, multilevel models using maximum likelihood estimation, k-means clustering, decision tress, and/or Bayesian hierarchical models to generate model-predicted data regarding future behavior of a provider.

Some embodiments of the present disclosure include measuring provider variation at key-clinical decision points. In some embodiments, the key-clinical decision points may include decisions that are known to be in advance of high-cost procedures and/or high-morbidity procedures such as arthroplasty, spinal laminectomy/fusion, cardias stenting, C-section, etc.

Embodiments of the present disclosure include a system for characterizing provider-specific variation at critical decision points (i.e., key-clinical decision points) within the patient journey, upstream from conventional procedure-triggered episodes of care. Furthermore, unlike traditional episode groupers restricting the horizon of evaluation to arbitrary time periods centered on a procedural event, the system of the present evaluates provider (i.e., physician) behavior and performance around the time of key discretionary clinical decision points driving health care expenditures and meaningful clinical and non-clinical outcomes. Conventional episode grouper systems and technologies assume equivalence with respect to the clinical necessity of individual procedure-triggered episodes. The system of the present disclosure, on the other hand, challenges this assumption, by rigorously evaluating system-, group-, and provider-level patterns in health care delivery benchmarked within individual health care markets.

One or more embodiments of the present disclosure include curating a provider network based on the performance scores of the providers within the provider network. In some embodiments, a provider assessment system may curate a provider network within a given region at the domain level. Furthermore, in some embodiments, a provider assessment system may enable a user to view how exchanges providers within the provider network may improve performance of the provider network. For instance, a provider assessment system may enable relatively easy and quick optimization of a provider network.

Moreover, because a provider assessment system can operate by interacting with a user via a graphical user interface on a mobile device, a provider assessment system is accessible to more users as more users will have access to a phone in comparison to a desktop and/or laptop. Furthermore, a provider assessment system removes steps typically necessary for creating a provider network. For instance, a provider assessment system automatically scores providers within a potential provider network, and automatically compares the potential provider network to existing provider networks based on performance scores acquired from claims data both within and between geographic boundaries. As a result, a provider assessment system does not require a substantial amount of information from a user unlike conventional systems. Thus, a provider assessment system provides quicker access to provider network performance in comparison to conventional system.

Additionally, a provider assessment system described herein improves a process of building provider networks. In particular, a provider assessment system provides performance scores so that users can build network to include the highest scoring providers and/or practice groups within a given region. Additionally, a provider assessment system provides automated comparisons of newly built provider networks and existing network enabling users to optimize provider networks in include the highest performing providers and to provide the best health care to patients. Furthermore, a provider assessment system increases a speed at which the provider networks can be identified and built, increases information available to users while building/creating a provider network, and enables more functionality as is described in greater detail herein.

FIG. 1 illustrates a schematic diagram of an environment 100 in which a provider assessment system may operate according to one or more embodiments of the present disclosure. As illustrated, the environment 100 includes a client device 102, at least one server 108 including a provider assessment system 104, a network 106, and one or more third-party system(s) 114. As used herein, the term "provider assessment system" refers to a system that assesses a provider's performance based on the provider's actions at key-clinical decision points within a patient's journey of care. For instance, as will be described in further detail below, a provider assessment system 104 may determine composite performance scores for a provider's performance in regard to effectiveness, appropriateness, and/or cost. The effectiveness score may reflect how well the provider's delivered care achieves an appropriate (e.g., right and/or desired) patient outcome. The appropriateness score may reflect whether or not the provider delivers care only when the care is necessary. The cost score may reflect where the provider delivers care efficiently at a reasonable cost. The scores are described in greater detail below in regard to FIG. 3. Furthermore, as is described in greater detail below, a provider assessment system 104 may curate provider networks based on the performance scores of providers within the network, and a provider assessment system 104 may provide for optimizing a provider network by including high performing providers within the provider network.

In some embodiments, the client device 102 may include an application 112 (e.g., a tool application) for enabling users to interact with a provider assessment system 104 in order to view provider performance scores and define provider networks based on provider performance scores. Furthermore, the application 112 may enable users to initiate curation of a given provider network and to optimize a provider network based on the provider performance scores. In particular, the client device 102 may execute one or more applications (e.g., application 112) for performing the functions of the various embodiments and processes described herein. For example, in some instances, the application 112 may be web application for determining and view provider performance scores and curating provider networks at, e.g., market and/or physician levels. In some embodiments, the application 112 may be local to the client device 102. In other embodiments, the application 112 may be stored and/or at least partially operated via a cloud computing service.

In one or more embodiments, the application 112 may be a native application installed on the client device 102. For example, the application 112 may be a mobile application that installs and runs on a mobile device, such as a smart phone or a tablet. The application 112 may be specific to an operating system of the client device 102. Further, the application 112 may be independent of a provider assessment system 104. Alternatively, the application 112 may be a client application that is associated with a provider assessment system 104 and configured to enable interaction directly with a provider assessment system 104 through the application 112.

A provider assessment system 104, the client device 102, and the third-party system(s) 114 may communicate via the network 106. In one or more embodiments, the network 106 includes a combination of cellular or mobile telecommunications networks, a public switched telephone network (PSTN), and/or the Internet or World Wide Web and facilitates the transmission of data between the client device 102 and a provider assessment system 104. The network 106, however, may include various other types of networks that use various communication technologies and protocols, such as a wireless local network (WLAN), a wide area network (WAN), a metropolitan area network (MAN), other telecommunication networks, or a combination of two or more of the foregoing networks. Although FIG. 1 illustrates a particular arrangement of the client device 102, the server 108, the third-party system(s) 114, and the network 106, various additional arrangements are possible. For example, the server 108 and, accordingly, a provider assessment system 104, may directly communicate with the client device 102, bypassing the network 106.

As illustrated in FIG. 1, a user 110 may interface with the client device 102, for example, to communicate with the server 108 and to utilize a provider assessment system 104 in order to view provider's performance scores, cause a provider assessment system 104 to curate provider networks by region and/or practice groups, and/or optimize provider networks based on curation data and provider performance scores. The user 110 may be an individual (i.e., human user), a business (e.g., employer), a group, or any other entity. Although FIG. 1 illustrates only one user 110 associated with the client device 102, the environment 100 may include any number of a plurality of users that each interact with the environment 100 using a corresponding client device.

The client device 102 may be any one or more of various types of computing devices. For example, the client device 102 may include a mobile device such as a mobile telephone, a smartphone, a PDA, a tablet, or a laptop, or a non-mobile device such as a desktop or another type of computing device. Additional details with respect to the client device 102 are discussed below with respect to FIG. 12.

In some embodiments, a provider assessment system 104 may include one or more systems, servers, and/or other devices for assessing provider performance and curating provider networks. Furthermore, a provider assessment system 104 may include and/or have access to one or more databases 116. For example, in some embodiments, a provider assessment system 104 may be implemented by a plurality of server devices that store, within the one or more databases, clinical and claims data, provider information and content, insurance information content, user information and content, medical evidence and clinical practice guidelines, and/or defined performance measures, and/or may facilitate querying any of the foregoing information and content to assess provider performance. As shown, in some embodiments, a provider assessment system 104 may include a database wherein the stores received claims data (described below), provider performance scores, analysis algorithms, etc.

The third-party systems 114 may include additional systems that interface with a provider assessment system 104. For example, in some embodiments, the third-party systems 114 may include third-party systems having and storing relatively large amounts of clinical and claims data (referred to herein collectively as "claims data"). As used herein, claims data may include records of medical events that are incurred by the patient visiting a healthcare professional (e.g., provider) or a facility in the ambulatory, outpatient, inpatient, home, and other environments where medical services may be delivered. Furthermore, claims data may have a claim line item (CLI) structure, where each claim of the claims data generally includes one or more CLIs. As is also known in the art, claims data may be recorded via various forms of data including client-defined codes, value fields (e.g., input fields), dates, system-specific codes, and standard codes (e.g., current procedural terminology (CPT) codes). In some embodiments, claims data merely includes electronic data that includes information regarding one or more instances of diagnosis, procedures, utilization, and/or combinations thereof and in combination with other things. The information may be organized into fields, but may be organized in other structures such that the fields may include fields, tags, etc.

Furthermore, the third-party systems may include systems having and storing complimentary data sources including standalone claims data, standalone clinical data derived from the electronic health record, linked claims-clinical data, and employer data, to develop, validate, and execute measures. As is described in greater detail below, the claims data may be used to build condition-specific patient cohorts (i.e., groups) which may serve as the foundation for the development of condition-specific episodes of care (referred to herein as "patient journey measurement"). Obtained from payers, individual claims represent transactions between providers and/or facilities and payers. As is described in greater detail below, a provider assessment system 104 may also incorporate both structured and unstructured clinical data derived from the electronic health records to supplement information contained in claims to support cohort development and validation, measure development and validation, and system execution.

In some embodiments, the third-party systems 114 may include one or more insurance providers (e.g., Blue Cross Blue Shield), employers sponsoring health plans, provider systems, health care organizations, hospitals, etc. In additional embodiments, the third-party systems 114 may include validations systems (e.g., systems associated with clinical experts and groups) for validating at least portions of an assessing process (e.g., performance measures) of a provider assessment system 104. As is described in further detail below, a provider assessment system 104 may analyze claims data received from the third-party systems to map generated and defined performance measures (e.g., defined measures to ascertain a providers' performance in a key-clinical decision point) to claims data and to determine composite scores of provider's performance relative the provider's peers individually, within a specialty, within a market, and/or within a network.

Figure 2:
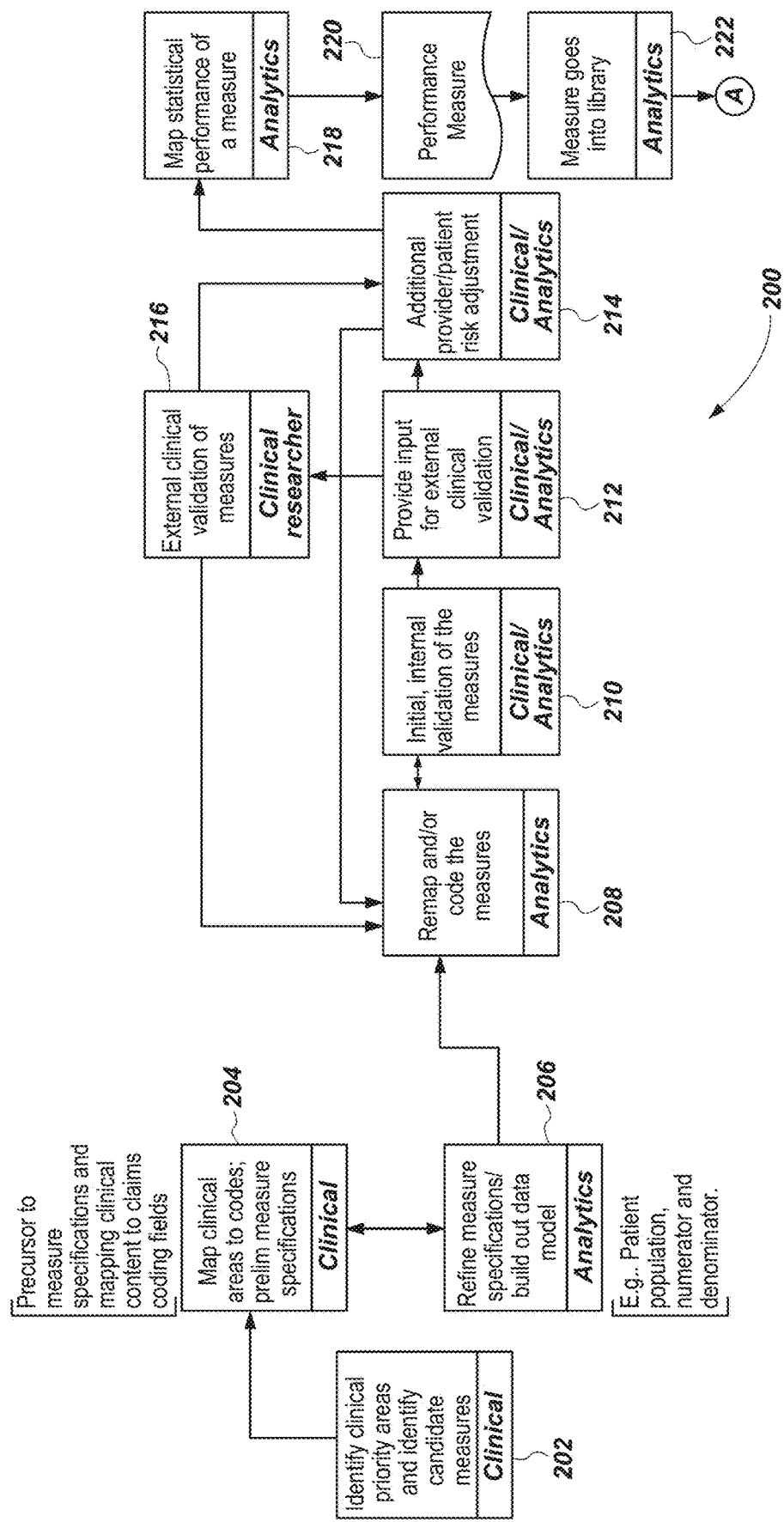
FIG. 2 illustrates a sequence flow diagram that a provider assessment system can utilize to create performance measures for measuring provider performance in accordance with one or more embodiments.

FIG. 2 illustrates a sequence-flow diagram 200 showing various acts of a provider assessment system 104 for developing and determining performance measures for assessing provider performance (e.g., measures utilized to assess a providers' action at a key-clinical decision point within a patient's journey relative to the provider's peers) and outputting provider performance scores in regard to at least appropriateness, effectiveness, and cost, as described herein. The performance scores are discussed in greater detail below in regard to FIG. 4. The provider assessment system 104 described in regard to FIG. 2 may be example embodiments of a provider assessment system 104 described in regard to FIG. 1.

As shown in act 202 of FIG. 2A, in some embodiments, a provider assessment system 104 may identify clinical priority areas (e.g., clinical categories) and may identify (e.g., define) candidate measures (e.g., measure concepts). As used herein, a "clinical area" may refer to a clinical category and/or patient condition and treatment plan within an area of practice typically performed and overseen by a provider, as defined above. For example, in some embodiments, a clinical area may include low-risk obstetrics, orthopedic surgery (joint care), orthopedic surgery (spinal care), cardiology, primary care, gastroenterology, pulmonology, etc. Furthermore, although specific clinical areas are described herein, one of ordinary skill in the art will readily recognize that clinical areas may include any area in which providers practice. In some embodiments, identifying clinical priority areas may include identifying clinical areas that typically include key-clinical decision points (e.g., whether or not to recommend surgery) in advance of high-cost procedures and/or high-morbidity procedures such as arthroplasty, spinal laminectomy/fusion, cardias stenting, C-section, etc. As will be discussed in further detail below, identifying clinical priority areas based on areas that include key-clinical decisions as described herein may enable isolating physician-level variation in inappropriate care and isolating individual provider performance that is benchmarked against peer providers in local markets and/or nationally. In some embodiments, identifying clinical priority areas may include identifying clinical priority areas based on subject matter expert input data, clinical literature, input from the clinical Advisory Board, etc. For instance, in some embodiments, the clinical priority areas may be user-defined by employers, provider networks, individuals (e.g., providers and/or clinical experts), etc. In view of the foregoing, a provider assessment system 104 may identify areas within medical practices that typically result in key-clinical decision points that have relatively significant consequences.

In one or more embodiments, identifying candidate measures (i.e., measure concepts) may include identifying candidate measures from existing measures (e.g., quality measures) from existing measure inventories of a provider assessment system 104 and/or third parties. For example, identifying candidate measures may include identifying relevant measures (e.g., measures that relate to the identified clinical priority areas described herein) within, for instance, measures inventories of the National Committee for Quality Assurance®, American Medical Association convened Physician Consortium for Performance Improvement®, National Quality Forum®, Centers for Medicare and Medicaid Services, Agency for Healthcare Research and Quality (e.g., Quality Indicators), Commission on Cancer, HEDIS®, etc. Furthermore, in some embodiments, identifying candidate measures may include identifying and/or augmenting already identified candidate measures with specialty-specific quality measures based on specialty society measure sets and clinical registries.

In one or more embodiments, identifying candidate measures includes analyzing claims data to identify a patient's journey (described in greater detail in regard to FIGS. 5 and 6) within a given clinical area, and based on the identified patient journey, a provider assessment system 104 may identify areas within the patient's journey where variation between journeys of different patients may be measurable. The areas within the patient's journey where variation in clinical practice and clinical performance between journeys of different patients that may be measurable may be identified as a candidate measure. In some embodiments, the candidate measures are identified automatically by a provider assessment system 104 based at least partially on identified key-clinical decision points within received claims data (e.g., claims data received from a third-party). In other embodiments, the candidate measures are at least partially identified (e.g., defined) via user input. In other words, the candidate measures are at least partially user-defined. As is discussed in greater detail below, the candidate measures may be directed to assessing an appropriateness of care provided by a provider, an effectiveness of care provided by the provider, and a cost of a care provided by the provider, as described herein.

Upon identifying the clinical priority areas and identifying candidate measures, a provider assessment system 104 maps (e.g., associates) the identified clinical priority areas and the identified candidate measures (e.g., clinical concepts tied to the candidate measures) to coding fields (e.g., current procedural terminology ("CPT") codes (e.g., the national coding set for physician and other health care professional services and procedures)) of claims data, as shown in act 204 of FIG. 2. As is known in the art, the CPT evidence-based codes accurately encompass the full range of health care services. Furthermore, as is known in the art, the CPT code descriptors are clinically focused and utilize common standards so that a diverse set of users can have common understanding across the clinical health care paradigm of claims data. In other words, a provider assessment system 104 associates the clinical priority areas and clinical concepts of the identified candidate measure to coding fields of claims data by generating a respective algorithm (i.e., specifications of the candidate measure) that identifies a numerator and a denominator clustered at the provider level in claims data. Put another way, a provider assessment system 104 specifies the candidate measure in terms of claims data as the algorithm. For example, a provider assessment system 104 defines the candidate measures as claims-based measures. Furthermore, a provider assessment system 104 may map the identified clinical priority areas and the candidate measures to any forms of data typically found within claims data (e.g., the forms of data described above in regard to FIG. 1) via the above-described manner.

In some embodiments, a provider assessment system 104 may map the identified clinical priority areas and the candidate measures to coding fields and/or other forms of data within the claims data via conventional data mapping methodologies. For example, a provider assessment system 104 may map the identified clinical priority areas and the candidate measures to coding fields and/or other forms of data within the claims data via field mapping and field value mapping methodologies. In field mapping, fields in the claims data are identified that correspond to each of the required fields. In field value mapping, for each field where applicable, a provider assessment system 104 determines the field value that corresponds to each possible value that may occur in the claims data, mapped to a clinical service or clinical event characterized in the patient journey. In some embodiments, a provider assessment system 104 may map the identified clinical priority areas and the identified candidate measures to coding fields and/or other forms of data within the claims data by creating eXtensible Stylesheet Language Transformations (XSLT Transform), by simultaneously evaluating actual data values of the coding fields of the claims data (e.g., data sources) using heuristics and statistics to automatically discover complex mappings between A) the identified clinical priority areas and the candidate measures and B) the coding fields and/or other forms of data within the claims data. In some embodiments, the foregoing methodologies are used to determine transformations between A) the identified clinical priority areas and the candidate measures and B) the coding fields and/or other forms of data within the claims data via discovering substrings, concatenations, arithmetic, case statements as well as other kinds of transformation logic. The foregoing methodologies may also determine data exceptions that do not follow the discovered transformation logic. In one or more embodiments, mapping the identified clinical priority areas and the candidate measures to coding fields may include semantic mapping.

As a non-limiting example, a provider assessment system 104 may identify orthopedic surgery as a clinical priority area and may identify a candidate measure as whether or not a patient received a pre-operative injection (i.e., whether or not a pre-operative joint injection was utilized), and upon identifying orthopedic surgery as the clinical priority area and whether or not a patient received a pre-operative injection as the candidate measure, a provider assessment system 104 may map the candidate measure to coding fields (e.g., CPT codes, ICD-10 codes, and/or input fields) of the claims data that may indicate whether or not the patient received a pre-operative injection (e.g., yield information regarding the candidate measure). Furthermore, the provide assessment system 102 may define the mapped coding fields as at least a portion of measure specifications of the candidate measure. For instance, the mapping data may comprise at least a portion of the candidate measure.

Upon mapping the identified clinical priority areas and the candidate measures to coding fields and/or data within claims data, a provider assessment system 104 may refine the preliminary measure specifications of a candidate measure to define specifications (e.g., mapped coding fields, etc.) of an initial performance measure, as shown in act 206 of FIG. 2. For instance, a provider assessment system 104 may refine the preliminary measure specifications of a performance measure based on a patient population, numerators, and denominators reflected in the claims data. As used herein, a numerators may reflect a number of patients that received a particular treatments (e.g., the provider acted in a certain way in regard to a key-clinical decision point), and the denominators may reflect a total number of patients exhibiting a same condition (e.g., knee pain) to which the particular treatments were prescribed.

Upon refining the measure specifications of the candidate measure and defining the initial performance measure, a provider assessment system 104 remaps the candidate measure to coding fields and codes the measure specifications as the initial performance measure, as shown in act 208. For instance, a provider assessment system 104 may remap (recode) the candidate measure to coding fields of the claims data to define the initial performance measure via any of the methods described above in regard act 204 of FIG. 2.

In response to coding the candidate measure as the initial performance measure, a provider assessment system 104 may perform an initial validation of the initial performance measure, as shown in act 210 of FIG. 2. For instance, a provider assessment system 104 may validate the initial performance measure against the claims data stored by a provider assessment system 104 within the database 116 of a provider assessment system 104. For example, a provider assessment system 104 may determine whether the defined specifications (e.g., the mapped coding fields of the claims data) of the initial performance measure yield information (e.g., desired information) relevant to the initial performance measure (e.g., the clinical concept and measure concept of the initial performance measure) when a provider assessment system queries the mapped coding fields of the claims data according to the specifications of the initial performance measure. For instance, a provider assessment system 104 may determine whether the mapped coding fields of the claims data identified in the specifications of the initial performance measure yield information relevant to the initial performance measure. As a non-limiting example, when the initial performance measure is related to whether or not a patient received a pre-operative injection during orthopedic surgery, a provider assessment system 104 may determine whether the defined specifications (e.g., mapped coding fields of the claims data) of the initial performance measure yield information relevant to whether or not a patient received a pre-operative injection during orthopedic surgery when the mapped coding fields are queried according to the specifications of the initial performance measure.

In some embodiments, a provider assessment system 104 may validate the initial performance measure (e.g., the specifications of the initial performance measure) against known positives or negatives within claims data. For instance, a provider assessment system 104 may validate the initial performance measure against claims data known to have coding fields and data relevant to the initial performance measure and/or may validate the initial performance measure against claims data known to not include coding fields and data relevant to the initial performance. Furthermore, a provider assessment system 104 may determine whether coding fields and data queried based on the specifications of the initial performance measure yield expected information based on the known claims data. In one or more embodiments, validating the initial performance measure may include an iterative process of validating the initial performance measure against known claims data. In some embodiments, a provider assessment system 104 may determine whether the initial performance measure satisfies a given threshold of correctly querying retrieving information relevant to the initial performance measure. For instance, a provider assessment system 104 may determine whether the specifications of the initial performance measure cause a provider assessment system 104 to correctly query and retrieve of information within the known claims data known to be relevant to the initial performance measure at an accuracy of 80%, 90%, 95%, or 99%.

Upon performing the initial validation of the initial performance measure, a provider assessment system 104 may provide for external clinical validation of the initial performance measure, as shown in act 212 of FIG. 2. For instance, in some embodiments, a provider assessment system 104 may send the specifications of the initial performance measure to one or more third-party systems for critique. As a non-limiting example, a provider assessment system 104 may send the specifications of the initial performance measure to one or more validation systems (e.g., systems associated with clinical experts and groups), physicians, clinical experts, clinical review boards, etc., for validating the specification of the initial performance measure.

Furthermore, as is described below, a provider assessment system 104 may receive critique information (e.g., scores) related to the accuracy and quality of the initial performance measures, as shown in act 216 of FIG. 2. In some embodiments, the external and/or internal clinical validation of the initial performance measure may include a physician-led clinical validation. In some embodiments, the physician-led clinical validation may include verifying that a condition-specific patient journey reflects an intended index patient (e.g., a patient whose disease or condition provides an index case (i.e., an instance of a disease or a genetically determined condition that is discovered first and leads to the discovery of others in a family or population)). Furthermore, the external clinical validation of the initial performance measure may include receiving data related to identified areas to improve precision of the initial performance measures. Moreover, the external clinical validation of the initial performance measure may enable rapid testing and iteration of new measure concepts developed by clinical experts.

In some embodiments, upon receiving the critique information (e.g., scores) via the external clinical validation, if adjustments are recommended in the critique information and/or via the validation process, a provider assessment system 104 may repeat acts 208-216 of FIG. 2 in regard to the initial performance measure until adjustments are no longer recommended. For instance, in some embodiments, the initial performance measures are modeled utilizing any of the methods described herein, scaled to ensure relative comparison between initial performance measures, collapsed into domain summary scores (e.g., between 0 and 100) using principal components analysis, and summarized for presentation to an end-user, as is described in greater detail herein.

Upon being externally validating the initial performance measure, a provider assessment system 104 may further adjust the initial performance measure (e.g., the specifications) based on provider input and/or patient risk, as shown in act 214 of FIG. 2. For instance, the initial performance measure (e.g., the specifications of the initial performance measure) may be subjected to hierarchical random effects modeling that statistically adjusts the specifications for patient-level comorbidity, socioeconomic indicators, and other potential confounders. As shown in FIG. 2, in some embodiments, adjusting the initial performance measure based on provider input and/or patient risk may result in recoding the initial performance measure and repeating acts 208-214. Furthermore, in some embodiments, act 214 may be performed later in the method/process. For instance, act 214 may occur at and/or after act 404 of FIG. 4, described below.

After performing the initial validation of the initial performance measure (e.g., act 208) and the external validation of the initial performance measure (e.g., act 216), a provider assessment system 104 may determine and/or map the statistical performance of the initial performance measures, as shown in act 218 of FIG. 2. In some embodiments, act 218 may include characterizing variation in statistical performance (i.e., measure performance) by provider within a geographical area to determine an extent to which the initial performance measure meaningfully discriminates between providers in the geographic area. In other words, act 218 includes characterizing an adequacy of the initial performance measure with respect to differentiating provider performance.

In response to determining and/or mapping the statistical performance of the initial performance measure, a provider assessment system 104 may define the performance measure and the specifications of the adjusted initial performance measure as a final performance measure and may store the final performance measure within the database 116 of a provider assessment system 104, as shown in acts 220 and 222 of FIG. 2. In some embodiments, a provider assessment system 104 may add the final performance measure to a library of performance measures within the database 116 of a provider assessment system 104. Example final performance measures for determining scores for an appropriateness score, an effectiveness score, and a cost score are depicted and listed in FIGS. 3A-3G.

In particular, FIG. 3A lists example final performance measures that may be utilized in scoring the performance of a provider within the clinical area of low-risk obstetrics. Additionally, FIG. 3B lists example final performance measures that may be utilized in scoring the performance of a provider within the clinical area of orthopedic surgery in regard to joint care. Moreover, FIG. 3C lists example final performance measures that may be utilized in scoring the performance of a provider within the clinical area of orthopedic surgery and neurosurgery in regard to spine care. Likewise, FIG. 3D lists example final performance measures that may be utilized in scoring the performance of a provider within the clinical area of cardiology. Also, FIG. 3E lists example final performance measures that may be utilized in scoring the performance of a provider within the clinical area of primary care. Furthermore, FIG. 3F lists example final performance measures that may be utilized in scoring the performance of a provider within the clinical area of gastroenterology. Finally, FIG. 3G lists example final performance measures that may be utilized in scoring the performance of a provider within the clinical area of pulmonology. Although specific final performance measures and clinical areas are depicted in FIGS. 3A-3G, one of ordinary skill in the art will readily recognize that any clinical area and any actions within the journey of patient care are included within the scope of the present disclosure.

Referring to FIGS. 3A-3G together, in some embodiments, the performance measures utilized to measure appropriateness may highlight key-clinical decision points in patient care that drive health care spending without concomitant improvement in patient outcomes. For instance, the performance measures highlight key-clinical decisions in patient care where there exists clinical equipoise between management options, evidenced by the absence of clear clinical practice guideline recommendations or inconsistent study findings in the clinical literature or in instances where the medical evidence has consistently shown that particular clinical services offer limited benefits. Discretionary decision-making is largely centered around the use of imaging, intervention, and/or hospitalization.

The measures utilized to measure effectiveness may be intentionally and custom developed to complement each other in the evaluation of overall provider performance in a holistic fashion. Like the development of appropriateness measures, the effectiveness measures are informed by clinical practice guidelines, medical literature, and expert opinion. Furthermore, provider assessment system 104 may highlight clinically meaningful outcome measures which map to effectiveness from the patient, provider, and/or health system perspectives.

The measure utilized to measure costs may measure total costs throughout a condition-specific patient journey, inclusive of all discretionary spending and over a clinically appropriate horizon. As is discussed below, the total costs of care are measured across a clinically appropriate horizon, permitting identification of overutilization, poor quality, and/or unit pricing as key cost drivers within condition-based episodes of care. Furthermore, providers, groups, and health systems may be compared to national and market-specific benchmarks to characterize cost performance and identify specific opportunities for improvement.

Figure 4:
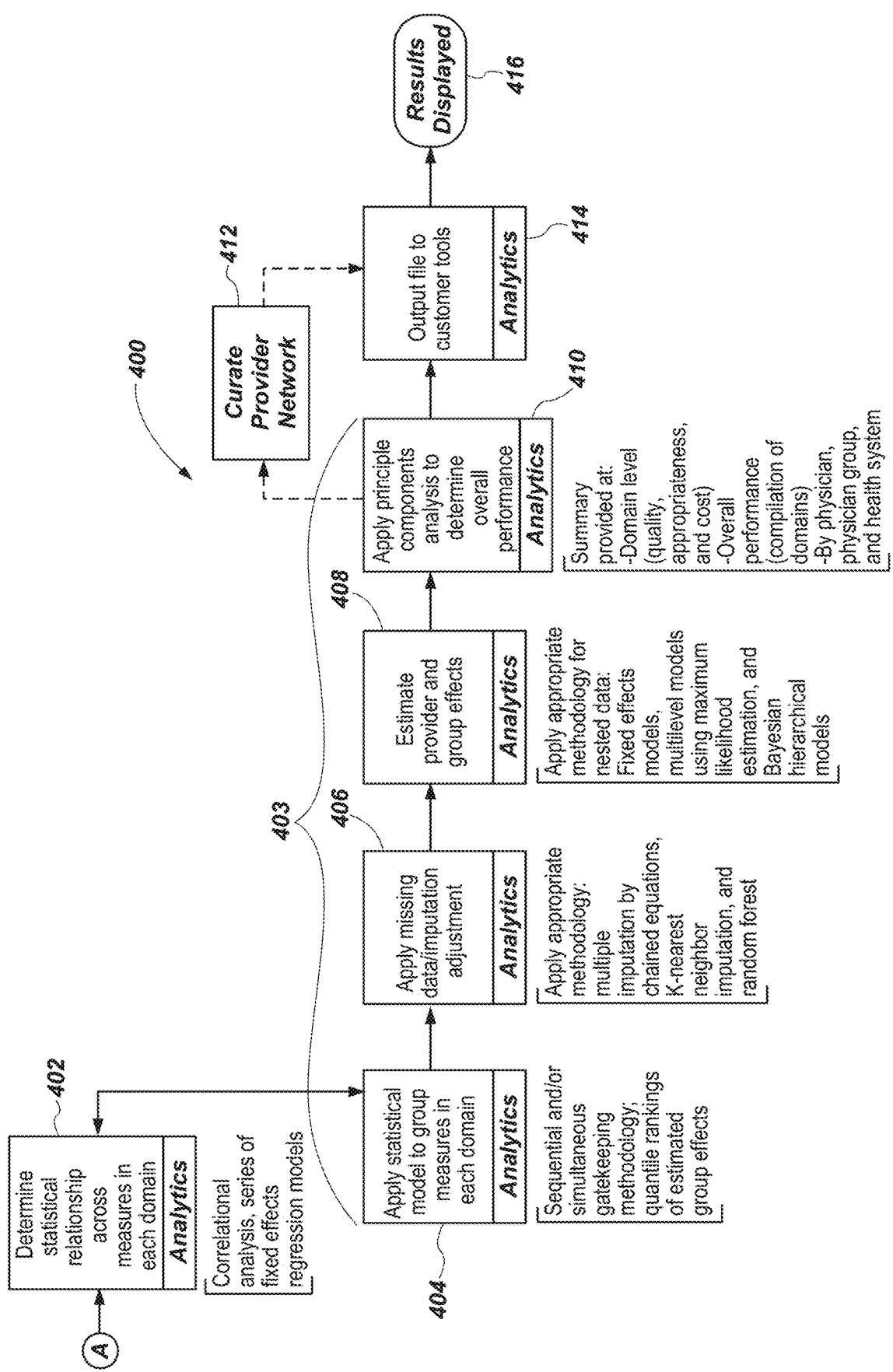
FIG. 4 illustrates a sequence flow diagram that a provider assessment system can utilize to determine performance scores for providers in accordance with one or more embodiments.

FIG. 4 is illustrates a sequence-flow diagram 400 showing various acts that a provider assessment system 104 may perform in order to determine performance scores for a given provider relative to the provider's peers individually, within a given specialty, a given market, and/or nationally according to one or more embodiments of the present disclosure. The sequence-flow diagram 400 further depicts acts for curating a provider network based on performance scores of the providers within the provider network. For instance, a provider assessment system 104 may perform one or more of the acts depicted in the sequence-flow diagram 400 to provide appropriateness scores, effectiveness scores, and cost scores of a provider relative to the provider's peers at a domain level (e.g., appropriateness, effectiveness, and/or cost).

Once the final performance measures are defined, applying the performance measures to the claims data to measure provider performance may result in a plurality of measure scores (i.e., a raw data output) with data representing provider performance (e.g., decisions) at decision points (e.g., key-clinical decision points) at a provider level, a group level, a network level, a hospital level, health system level, etc., depending on a aggregation method applied to the measure scores (i.e., raw data output). For instance, each measure score of the plurality of measure scores may include data regarding a single decision of a provider at a decision point reflected in the claims data. Utilizing the measure scores of providers within, e.g., a given specialty, as shown in FIG. 4, a provider assessment system 104 may determine statistical relationships between performance measures (e.g., the final performance measures) within the library of performance measures in each domain based on the measure scores, as shown in act 402 of FIG. 4. For instance, a provider assessment system 104 may determine (e.g., identify) correlations and/or relationships between performance measures within a given clinical area (e.g., obstetrics (low-risk pregnancy), orthopedics (joint care), orthopedics (spine care), cardiology, primary care, gastroenterology, pulmonology, etc.). In some embodiments, a provider assessment system 104 may determine statistical relationships between performance measures by applying correlation analyses and/or statistical techniques (e.g., bivariate correlation analyses, regression analyses, path analyses, canonical correlation analyses, etc.) to the measures scores (e.g., raw data output) for each provider within a given domain. In one or more embodiments, a provider assessment system 104 may determine statistical relationships between performance measures by applying a series of fixed effects regression models to the measure scores of each provider within a given domain.

Upon determining statistical relationships between the performance measures, a provider assessment system 104 may apply a series of analyses and/or models to the measure scores to determine composite performances scores for a provider at the domain level (appropriateness, effectiveness, and/or cost), as shown in act 403 of FIG. 4. For example, as is described in further detail below, a provider assessment system 104 may determine one or more composite performances scores associated with effectiveness, appropriateness, and cost, as described herein, at a network level, physician level, practice group level, hospital, and/or health system level.

In some embodiments, applying the series of analyses and/or models to the measure scores may include applying one or more statistical models to the measure scores of providers, as shown in act 404 of FIG. 4. For example, a provider assessment system 104 may apply one or more gatekeeping strategies to the measure scores. In some embodiments, a provider assessment system 104 may apply one or more gatekeeping strategies to the measure scores that does not require all primary effects to be significant. As a non-limiting example, a provider assessment system 104 may apply one or more sequential and/or simultaneous gatekeeping methodologies to the measure scores. For instance, a provider assessment system 104 may apply one or more serial gatekeeper methodologies, parallel gatekeeper methodologies, tree-structured gatekeeper methodologies, etc., to the measure scores. Furthermore, a provider assessment system 104 may apply one or more of Bonferroni tests, weighted Simes tests, and/or weighted resampling-based tests to the measures scores. By applying one or more sequential and/or simultaneous gatekeeping methodologies to the measures scores, a provider assessment system 104 may determine quantile rankings of estimated group effects of the measure scores. In some embodiments, act 404 is optional and may not be performed in every embodiment.

Additionally, in one or more embodiments, applying the series of analyses and/or models to the measure scores may include imputing data for the measure scores, as shown in act 406 of FIG. 4. For instance, a provider assessment system 104 may impute data for missing data (e.g., values) within the measures scores. In some embodiments, a provider assessment system 104 may impute data for the measure scores to improve the data sets (e.g., the raw data outputs of the measures and/or the claims data) via multivariate imputation by chained equations (MICE), K-nearest neighbor (KNN) imputation, and/or random forest imputation methods. Furthermore, a provider assessment system 104 may impute data for the measure scores via deep learning. For instance, a provider assessment system 104 may impute data via deep learning including machine-learning models using deep neural networks to impute missing values within the measure scores.

Furthermore, in one or more embodiments, applying the series of analyses and/or models to the measure scores may include estimating provider and provider group effects on the measures scores, as shown in act 408 of FIG. 4. For instance, a provider assessment system 104 may fit a predictive model to the measures scores that enables a provider assessment system 104 to predict how a provider would act within a confidence interval given a key-clinical decision point within a patient's journey. For instance, a provider assessment system 104 may analyze and/or process the measure scores (e.g., the raw output data resulting from applying the final performance measures to the claims data)

via fixed effects models, multilevel models using maximum likelihood estimation, k-means clustering, decision tress, and/or Bayesian hierarchical models to determine the effects that individual providers and/or provider groups have on the measure scores of a given practice group. Furthermore, by fitting a predictive model to the measure scores, a provider assessment system 104 may generate model-predicted measure scores. As will be understood in the art, determining the effects that individual providers and/or provider groups on the raw output data and fitting a predictive model to the measure scores may enable a provider assessment system 104 to penalize the effect (e.g., minimize the effect and/or compensate for the effect) of small data samples of individual providers and/or provider groups and/or outliers.

Moreover, in one or more embodiments, applying the series of analyses and/or models to the measure scores may include generating and summarizing an overall provider performance of a provider at a domain level as composite performance scores, as shown in act 410 of FIG. 4. For instance, given the measure scores and/or model predicted measure scores resulting from applying the final performance measures to the claims data and as adjusted and augmented via acts 404-408, a provider assessment system 104 may utilize an orthogonal transformation to convert the measure scores (e.g., a set of observations of possibly correlated numerical values) into the composite performance scores, including, the appropriateness score, the effectiveness score, and the cost score, as described herein. As a non-limiting example, a provider assessment system 104 may apply any principal component analysis known in the art to the measures scores at a provider level. As discussed above in regard to FIG. 1, the appropriateness score may reflect whether or not a given provider delivers care only when the care is necessary, the effectiveness score may reflect how well the given provider's delivered care achieves an appropriate (e.g., right) patient outcome, and the cost score may reflect whether the given provider delivers care efficiently at a reasonable cost. In some embodiments, a provider assessment system 104 may generate the composite performance scores at the domain level and/or at an overall level (e.g., a compilation of domains for a provider, a given provider group, a provider network, or an insurance network). Furthermore, a provider assessment system 104 may generate the composite performance scores by a physician group level and/or a health system level (e.g., a hospital or group of hospitals level). Upon generating the composite scores according to any of the manners described above, a provider assessment system 104 may store the composite scores within the database 116 of a provider assessment system 104.

In some embodiments, the composite scores may include a percentage score (e.g., a number between 1 and 100). In some instances, the score may indicate a better score when the percentage is higher. In other embodiments, the percent may indicate a percentage within which the provider falls (e.g., a top percentage or bottom percentage) of a given specialty, a market, a network, etc. As is described above, the performance scores of a given provider may be relative to the performance scores of the provider's peers. The scores are described in greater detail below in regard to FIGS. 7A-7H.

As discussed above, in some embodiments, a provider assessment system 104 may apply a predictive model to the measure scores and may predict future provider behavior. In such instances, a provider assessment system 104 may generate predictive data regarding the composite scores. For instance, a provider assessment system 104 may predict if the next procedure performed by the provider will be medically necessary, high quality, and at an appropriate cost. As a non-limiting example where a provider has been given the composites scores of Appropriateness (9%), Effectiveness (15%), and Cost (18%), a provider assessment system 104 may generate a message for display on a client device stating "the next time this provider performs a hip replacement, there is a 15% chance that the provider will do a good job, a 9% chance that the procedure will be medically necessary, and an 18% chance that the cost will be appropriate." Furthermore, although specific probabilities are mentioned and associated with the composite scores herein, the present disclosure is not so limited; rather, in some embodiments, the composite scores may not reflect specific probabilities, and the composite scores may reflect scaled assessments to enable holistic evaluation of performance and may not imply a likelihood of a specific outcome.

Additionally, in some embodiments, upon generating the composite performance scores and/or predictive data, a provider assessment system 104 may curate a provider network based at least partially on the composite scores, as shown in act 412 of FIG. 4. For instance, a provider assessment system 104 may determine the composites performance scores for a plurality (e.g., all or most) of providers within a given provider network (e.g., providers within a given specialty and region), and a provider assessment system 104 may curate (e.g., rank) the provider network based on the determined performance scores of the plurality of providers. In additional embodiments, a provider assessment system 104 may curate one or more of a provider group, a group of providers within a given market (e.g., geographical area), providers included within a health system (e.g., hospital or group of hospitals), and/or providers within a given specialty and given market. Furthermore, in one or more embodiments, a provider assessment system 104 may curate according to a specialty and region. In some embodiments, curating a provider network is optional. In other words, act 412 is not required in every embodiment. Curating provider networks is described in greater detail below in regard to FIGS. 7A-7H.

Upon determining the composite performance scores and/or curating a provider network, a provider assessment system 104 generates and outputs performance data for display within the application 112 (e.g., tool application) of the client device 102, as shown in act 414 of FIG. 4. For instance, a provider assessment system 104 may generate and output a data package including information related to the determined composite performance scores of providers and/or a curation of the provider network for display within the application 112 of the client device 102. The application 112 and graphical user interface of the application 112 is described in greater detail below in regard to FIGS. 7A-7H.

In response to generating and outputting the performance data, a provider assessment system 104 may cause the performance data to be displayed within the application 112 of the client device 102, as shown in act 416 of FIG. 4. Displaying the performance data within the application is described in greater detail below in regard to FIGS. 7A-7H.

Referring to FIGS. 2-4 together, in some embodiments, a provider assessment system 104 may continuously be receiving updated claims data, and a provider assessment system 104 may be continuously learning (e.g., the machine-learning models of a provider assessment system may be continuously learning) and adjusting performance scores to reflect changing behaviors of providers quickly.

Figure 5:
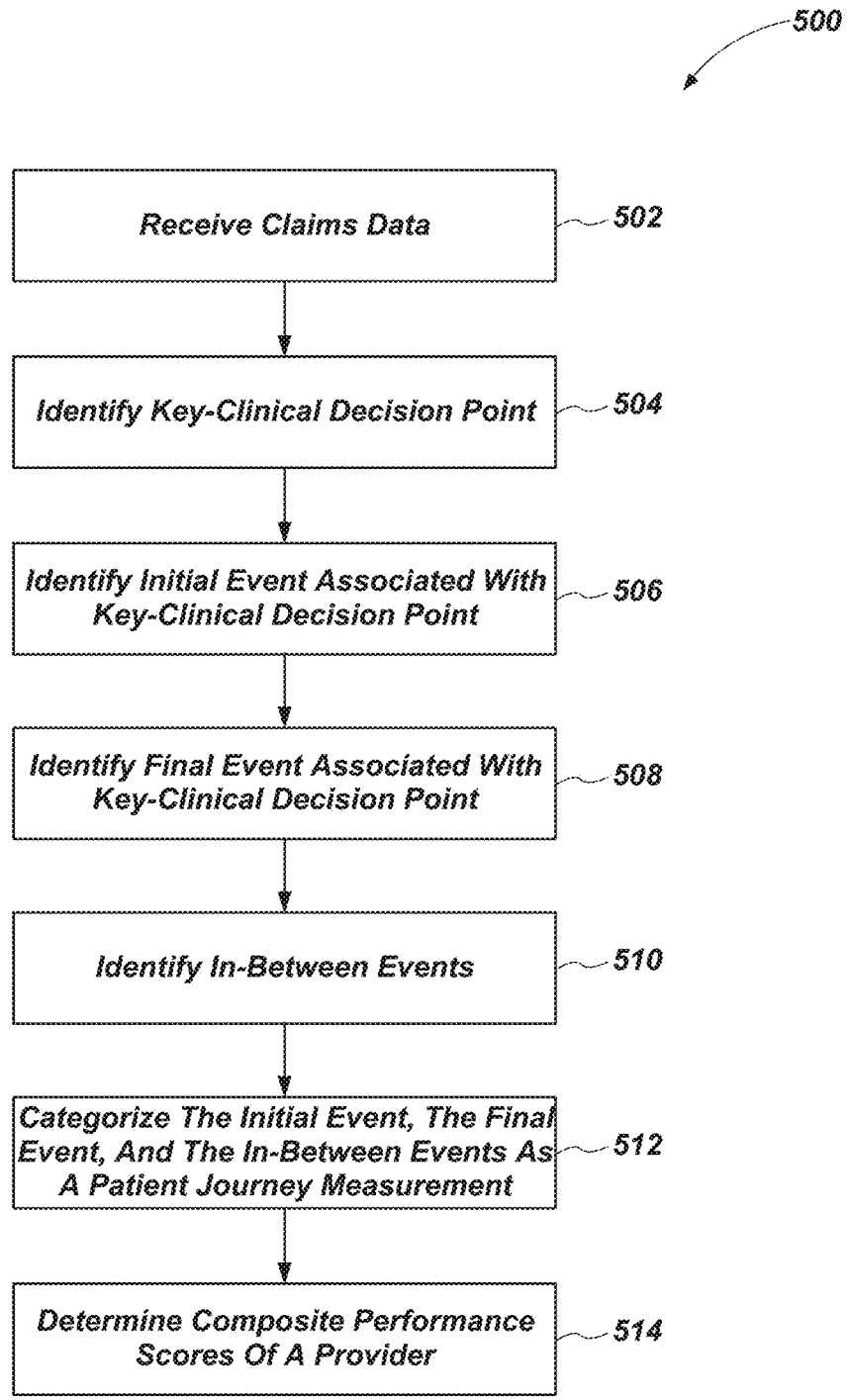
FIG. 5 illustrates a sequence flow diagram that a provider assessment system can utilize define a patient journey measurement in accordance with one or more embodiments of the present disclosure.

FIG. 5 includes a flow chart depicting a method 500 of defining a condition-based journey measurement of a patient according to one or more embodiments of the present disclosure. In some embodiments, the method 500 may include receiving claims data 502, as shown in FIG. 5. For instance, a provider assessment system 104 may receive claims data from a third-party system 114. As noted above, the third-party system 114 may include one or more insurance providers (e.g., Blue Cross Blue Shield), employers sponsoring health plans, provider systems, health care organizations, hospitals, etc.

Furthermore, the method 500 may include identifying at least one key-clinical decision point associated with the patient, as shown in act 504 of FIG. 5. For instance, a provider assessment system 104 may analyze the claims data with or without user input to identify a point within a patient's journey when the provider made a clinical decision that did or could have resulted in subsequent relatively high-cost procedures and/or high-morbidity procedures. In some embodiments, the key decision point may be identified through review of clinical literature, clinical practice guidelines, and input from experts instead of and/or in addition to evaluation of the claims data.

Additionally, the method 500 may include further analyzing the claims data to identify an initial event associated with the key-clinical decision point, as shown in act 506. For instance, a provider assessment system 104 may analyze the claims data to identify an earliest event indicated in the claims data that is clinically related (based on latest scientific guidelines, medical evidence, clinical practice, guidelines, and/or healthcare guidelines) to the key-clinical decision point. For example, a provider assessment system 104 may identify a diagnosis of the condition to which the key-clinical decision point is regarding and/or a diagnosis of a relating condition. As a non-limiting example, in the regard to a key-clinical decision point concerning whether or not to perform spinal fusion, a provider assessment system 104 may analyze the claims data to identify a diagnosis of back pain.

Likewise, the method 500 may include analyzing the claims data to identify a final event associated with the key-clinical decision point, as shown in act 508 of FIG. 5. For example, a provider assessment system 104 may analyze the claims data to identify a most recent event indicated in the claims data that is clinically related to the key-clinical decision point. For instance, a provider assessment system 104 may identify a final treatment related to the condition to which the key-clinical decision point is regarding. As a non-limiting example, in the regard to a key-clinical decision point concerning whether or not to perform spinal fusion, a provider assessment system 104 may analyze the claims data to identify a final treatment of physical therapy, or a decision to perform a subsequent surgery, etc. In some embodiments, the final event may include clinical improvement, clinical deterioration, a need for additional management, etc.

Moreover, the method 500 may include analyzing the claims data to identify in-between events, as shown in act 510 of FIG. 5. For example, a provider assessment system 104 may analyze the claims data to identify events indicated in the claims that that are clinically related to the key-clinical decision point and fall between the initial event and the final event within a timeline. As a non-limiting example, in the regard to a key-clinical decision point concerning whether or not to perform spinal fusion, provider assessment system 104 may analyze the claims data to identify in-between events including, for example, an x-ray, a surgical referral, injections, spinal fusion surgery, hospital discharge, post-acute care discharge, readmission, physical therapy, etc.

The method 500 may further include categorizing the initial event, the final event, and the in-between events and any claims data related to those events as a patient journey measurement, as shown in act 512 of FIG. 5. For example, upon identifying the initial event, the final event, and the in-between events and any claims data related to those events, a provider assessment system 104 may generate a data package including data representing the initial event, the final event, and the in-between events and any claims data related to those events, and a provider assessment system 104 may categorize the data package as the patient journey measurement.

In view of the foregoing, the method 500 and act 512 of FIG. 5 may enable a provider assessment system 104 to characterize a patient experience from a diagnosis of a condition (e.g., knee, hip, and/or back pain) and through treatment and to characterize provider-level variation in the level (e.g., intensity) of care delivery conventionally unexplained by patient-level factors. The patient journey measurement is described in further detail below in regard to FIG. 6. Additionally, the patient journey measurement of the present disclosure may provide advantages over conventional measurements (e.g., conventional episodes of care measurements). For instance, the patient journey measurement may provide a holistic view that begins before an initial diagnosis of a condition and promotes clinical consistency by enabling similar comparisons within similar cohorts of patients. Furthermore, the patient journey measurements holistically capture key-clinical decision points in advance of relatively high-cost procedures and/or high-morbidity procedures, such as, for example, arthroplasty, laminectomy, and/or spinal fusion. Moreover, the patient journey measurements enable a provider assessment system 104 to isolate provider-level variation in inappropriate care, benchmarked against peers in a given market (e.g., local or national).

In some embodiments, two or more of the initial event, the final event, and the in-between events may be associated with different specialties. For example, in one or more embodiments, the patient journey measurement may span two or more specialties. The relationship between specialties, for example timing of orthopedic surgery referral by primary care, may be used to characterize provider performance specifically with respect to the appropriateness (timing) of specialist referral.

Referring still to FIG. 5, the method 500 may include determining composite performance scores of a provider indicated in the claims data, as shown in act 514 of FIG. 5. For instance, based on the patient journey measurement, a provider assessment system 104 may utilize any of the performance measures described herein to determine composite performance scores that reflect the patient journey measurement. For instance, each performance score may include a score considering (e.g., reflecting) the entirety of the patient journey measurement. For example, in some embodiments, each performance score may be specific and/or isolated to the patient journey measurement. The composite performance scores may include any of the composite performance scores (e.g., appropriateness, effectiveness, and cost) described above, and the composite performance scores may be determined via any of the manners described above. Furthermore, the composite performance scores may be related to the key-clinical decision point(s) of the patient journey measurement.

Figure 6:
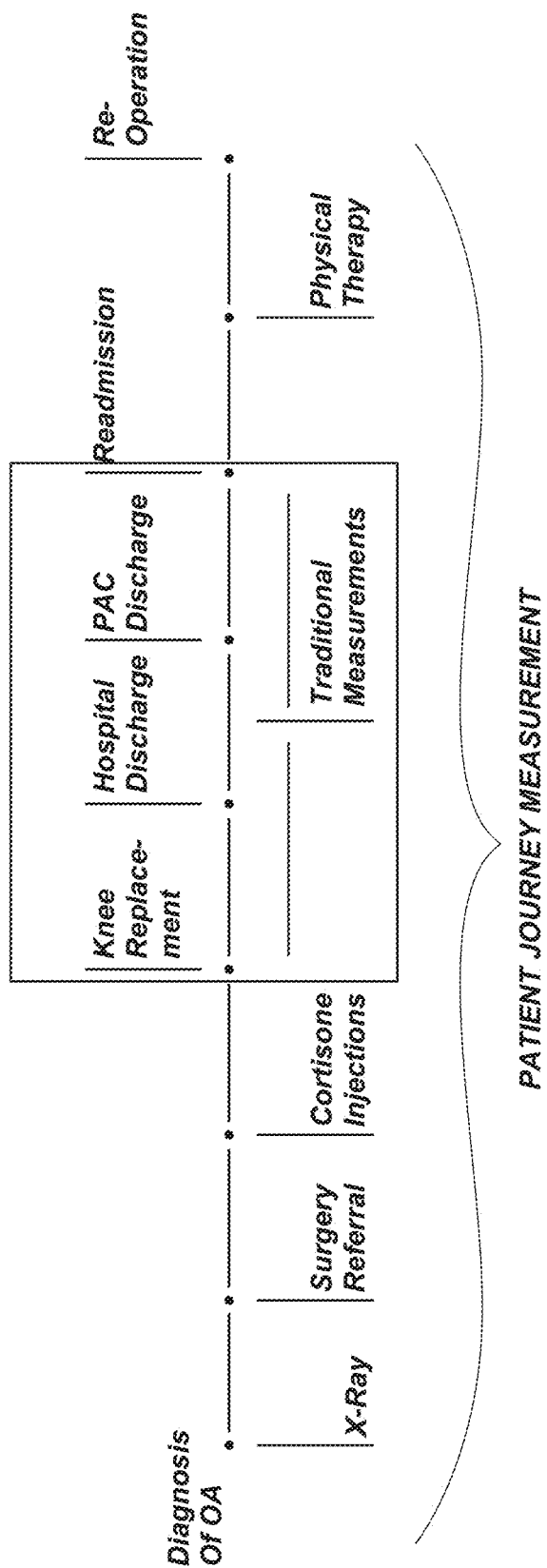
FIG. 6 depicts a patient journey measurement according to one or more embodiments of the present disclosure in comparison to a conventional episode measurement.

FIG. 6 is a schematic diagram showing a patient journey measurement (as described above in regard to FIG. 5) of the present disclosure in comparison to traditional episode of care measurements. As shown, the patient journey measurement of the present disclosure encompasses and accounts for significantly more events and a significantly longer period of time in comparison to conventional episode of care measurements. Furthermore, the patient journey measurement provides the advantages described above in regard to FIG. 5.

FIGS. 7A-7H illustrate a flow of user interfaces including features of the environment 100 according to an embodiment of the present disclosure. As will be described in more detail below, the components of the environment 100 as described in regard to FIGS. 1-6 may provide, alone and/or in combination with the other components, one or more graphical user interfaces ("GUIs"). A GUI typically includes one or more display regions and active/activatable regions. As used in this disclosure, a display region is a region of a GUI which displays information to a user. An activatable region is a region of a GUI, such as a button, slider, or a menu, which allows the user to take some action with respect to the GUI (e.g., if manipulated). Some display regions are also activatable regions in that the activatable regions display information and enable some action that may be taken by a user. In a contact-sensitive GUI, contacting a contact-sensitive area associated with an activatable region may activate that region (e.g., selecting a GUI button). Activatable regions may be displayed as GUI elements/objects, for example, buttons, sliders, selectable panes, menus, etc., all of various shapes and sizes. In particular, the components (e.g., the activatable regions of the GUI) may allow a user 110 to interact with a collection of display elements for a variety of purposes. In particular, FIGS. 4A-4L and the description that follows illustrate various example embodiments of the user interfaces and features that are in accordance with one or more embodiments of the present disclosure.

Figure 7A:
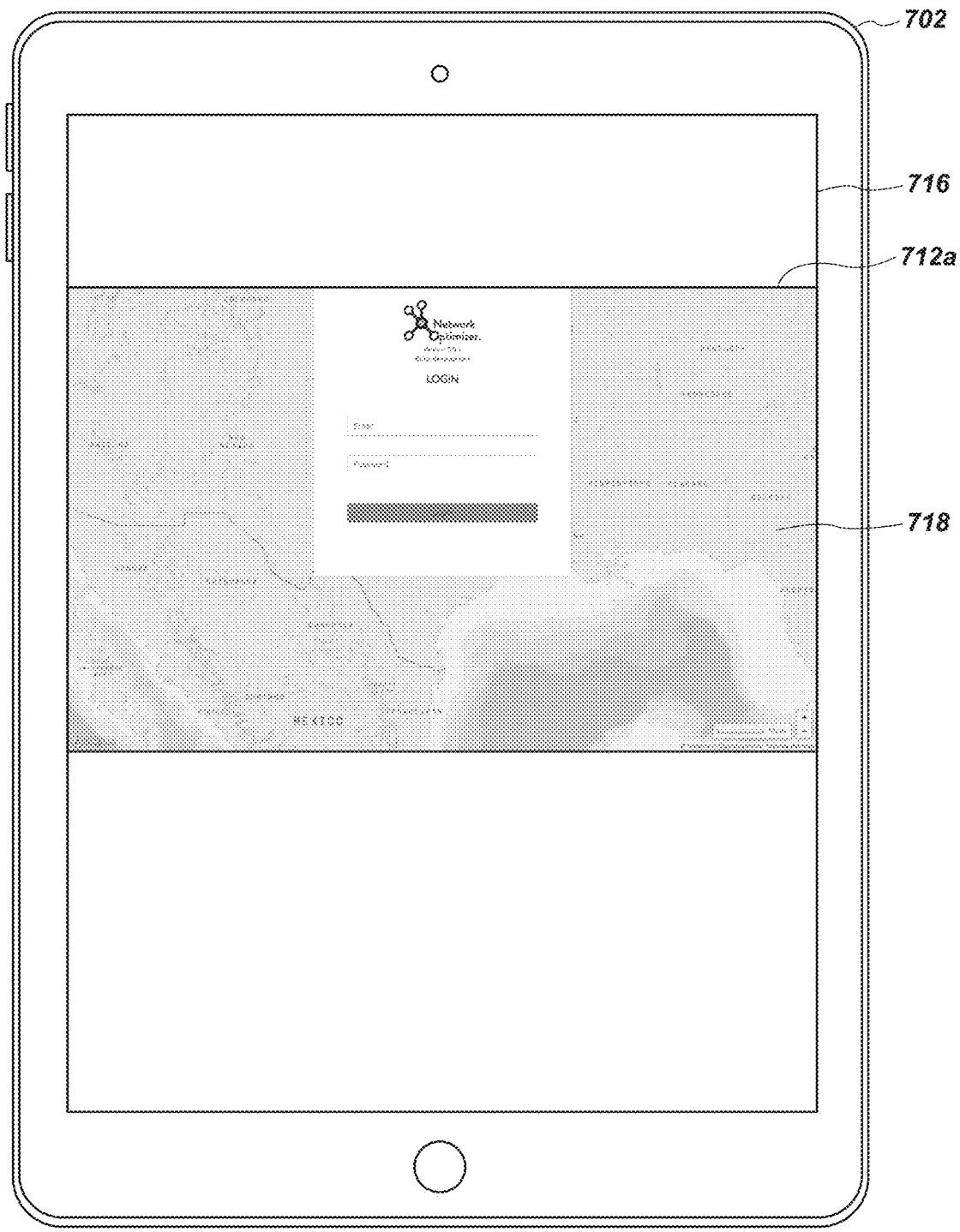
FIGS. 7A-7H illustrate a plurality of schematic representations of graphical user interfaces of a tool application of a provider assessment system that user can utilize to view performance scores of providers and curate provider networks according to one or more embodiments of the present disclosure.

For example, FIG. 7A illustrates a client device 702 of a provider determination system 104 user (e.g., the user 110 of FIG. 1) that may implement one or more of the components or features of the environment 100. As shown in FIG. 7A, in some embodiments, the client device 702 is a tablet device. In some embodiments, the client device 702 is a handheld device, such as a mobile phone device (e.g., a smartphone). As used herein, the term "handheld device" refers to a device sized and configured to be held/operated in a single hand of the user 110 and/or worn and operated by one or more hands of the user 110. In additional or alternative examples, however, any other suitable computing device, such as, but not limited to, a larger wireless device, laptop or desktop computer, a personal digital assistant device, and/or any other suitable computing device may perform one or more of the processes and/or operations described herein.

The client device 702 includes a touch screen display 716 that may display user interfaces. Furthermore, the client device 702 receives and/or detects user input via the touch screen display 716. As used herein, a "touch screen display" refers to the display of a touch screen device. In one or more embodiments, a touch screen device may be the client device 702 with at least one surface upon which a user 110 may perform touch gestures (e.g., a laptop, a tablet computer, a personal digital assistant, a media player, a mobile phone, etc.). Additionally or alternatively, the client device 702 may include any other suitable input device, such as a touch pad or those described below with reference to FIG. 12.

Additionally, FIGS. 7A-7H show example GUIs of a tool application of a provider assessment system 104 for providing a variety of services including determining and viewing provider performance scores, comparing providers and/or provider groups based on performance scores, determining provider variation, comparing provider network performance scores, curating provider networks, optimizing provider networks, building provider networks, and improving provider networks according to any of the manners described above. For instance, as shown in FIG. 7A, the touch screen display 716 of the client device 702 displays a tool application GUI 712a. The tool application GUI 712a displays introduction login GUI 718 showing a login GUI including input fields for inputting user credentials (e.g., email, username, password, etc.) to access a provider assessment system 104.

Figure 7B:
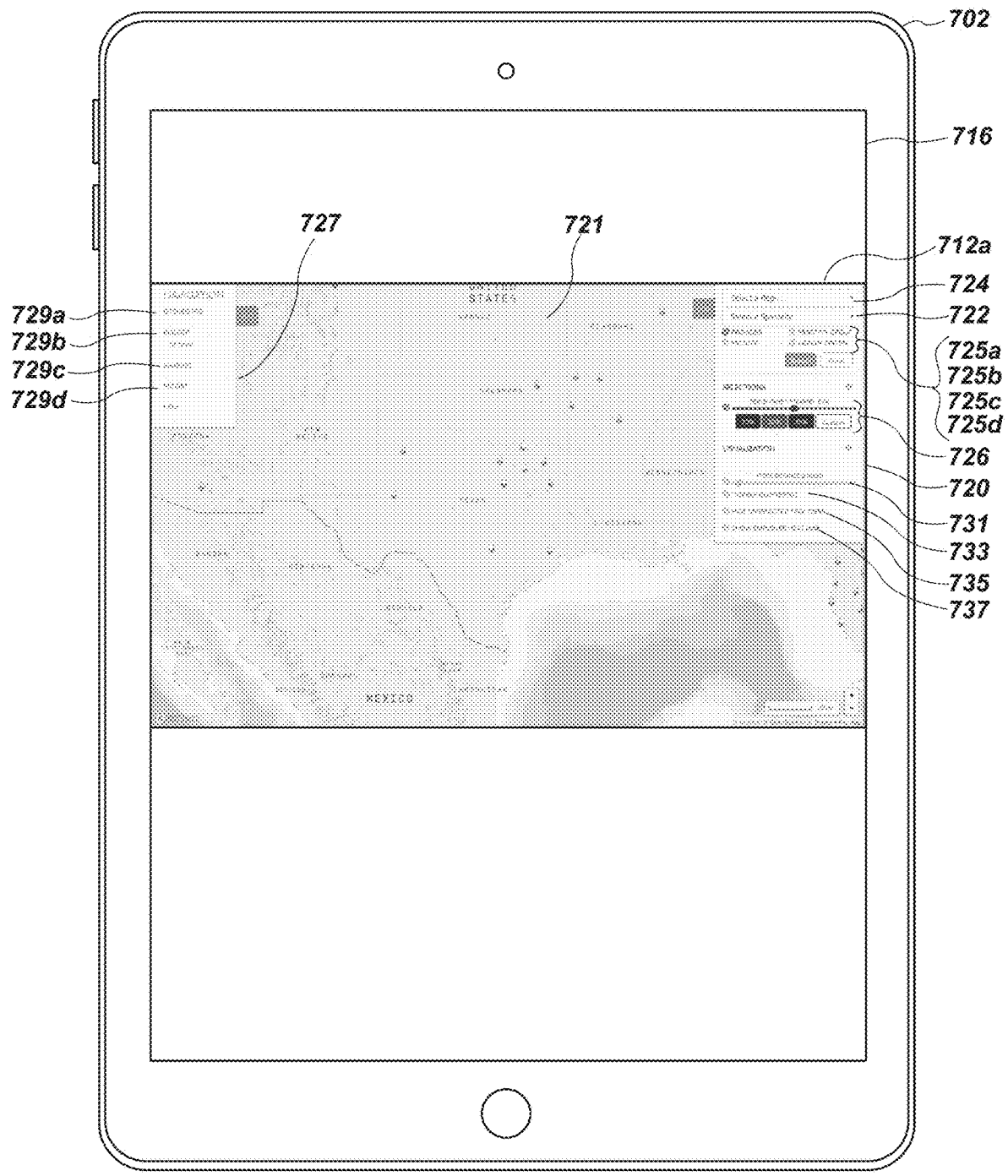

FIG. 7B shows a dashboard GUI 720 for selecting specialties (e.g., practice areas) and regions when viewing and comparing provider performance scores within the tool application of a provider assessment system 104. In some embodiments, the dashboard GUI 720 may include a map GUI 721 for displaying a selected region and depicting providers via selectable elements and based on geographic location, as is described in greater detail below. Furthermore, the dashboard GUI 720 may include a plurality of selectable elements 722, 724 for selecting a specialty and a region of providers/practice groups/facilities/health systems to compare based on performance scores. In some embodiments, the plurality of selectable elements 722, 724 may include drop-down menus for selecting the regions and specialties. Additionally, the dashboard GUI 720 may include selectable elements 725a, 725b, 725c, 725d for selecting whether to compare and view providers, practice groups, facilities, and/or health systems. As is discussed above, in some embodiments, the dashboard GUI and associated content windows may compare and curate the providers, practice groups, facilities, and/or health systems based on any of the performance scores and/or composite scores described herein. Moreover, the dashboard GUI 720 may include a selectable element 726 for selecting a benchmark (e.g., a top percentage) relative to which the providers/practice groups/facilities/health systems (selected based on the specialty and region) are to be scored.

The dashboard GUI 720 may further include a navigation window 727 having a plurality of selectable elements 729a, 729b, 729c, 729d for navigating within the tool application of the provider assessment system 104. Additionally, the dashboard GUI 720 may an employer distance selectable element 731 for selecting a radius from which providers/practice groups/facilities/health systems need to be in order to be included depicted within the map GUI 721. Furthermore, the dashboard GUI 720 may include a clustering selectable element 733 to enable and/or disable clustering of providers/practice groups/facilities/health systems within the map GUI 721. Moreover, the dashboard GUI 720 may include a hide unselected providers selectable element 735 for hiding unselected providers/practice groups/facilities/health systems within the map GUI 721. Also, the dashboard GUI 720 may include an employee heat map selectable element 737 for causing employees of an employer to be depicted within the map GUI 721 as a heat map, as depicted and described in regard to FIG. 7D.

Figure 7C:
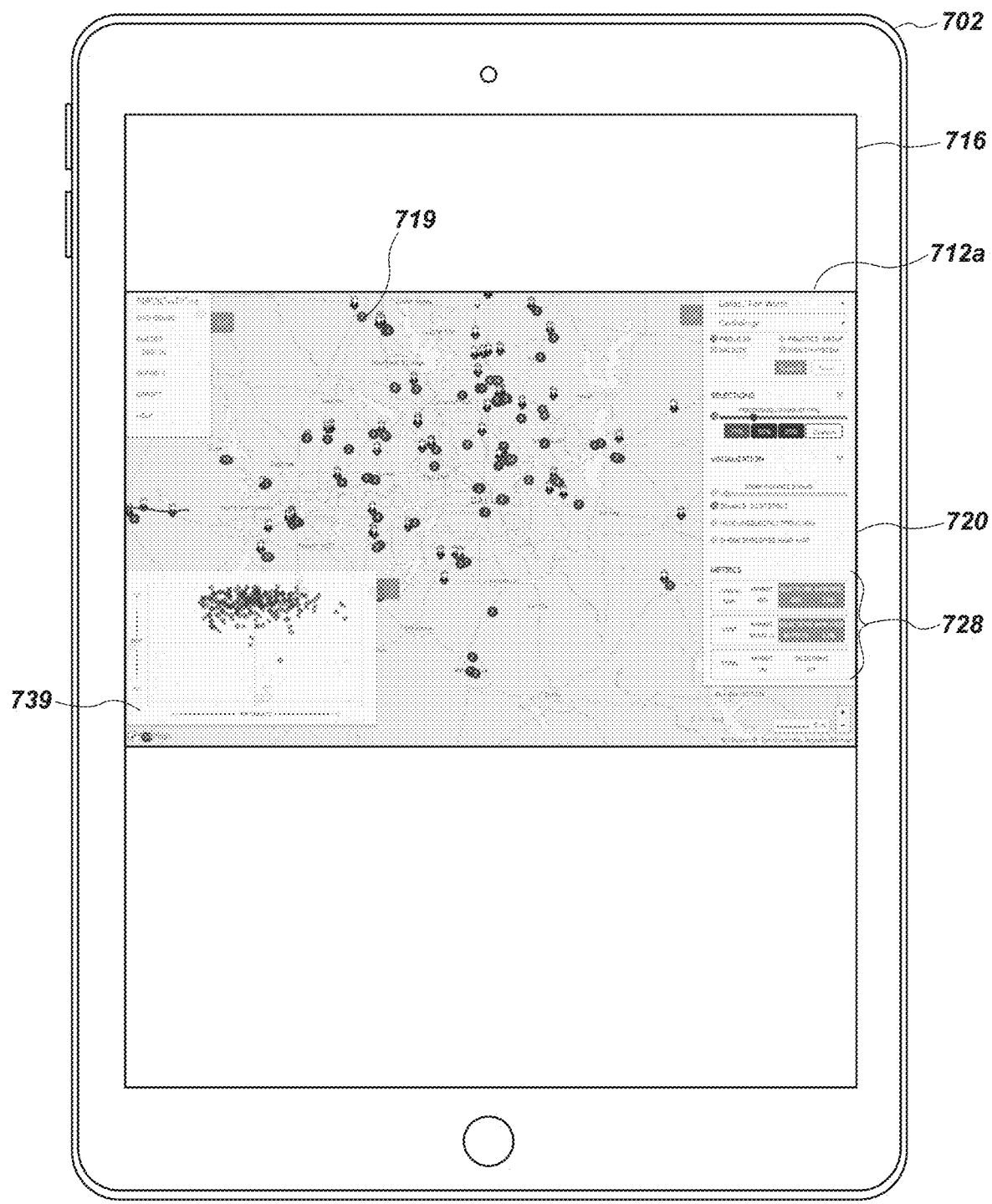

FIG. 7C shows the dashboard GUI 720 with a region and specialty selected for providers. As shown in FIG. 7C, when a region and specialty is selected, the dashboard GUI 720 may include one or more provider elements 719 representing providers (or in other embodiments, practice groups, facilities, and/or health systems) and a metrics content window 728, which shows performance and costs scores of a selected provider network relative to a market. Furthermore, when a region and specialty is selected, the dashboard GUI 720 may include a performance graph 739 plotting providers based on performance score (quality score) (appropriateness+effectiveness) and cost score relative to other providers within the market. Moreover, the provider elements 719 may be individually selectable to add to a provider network and/or display details regarding the individual provider, as is described in further detail below in regard to FIG. 7G.

Figure 7D:
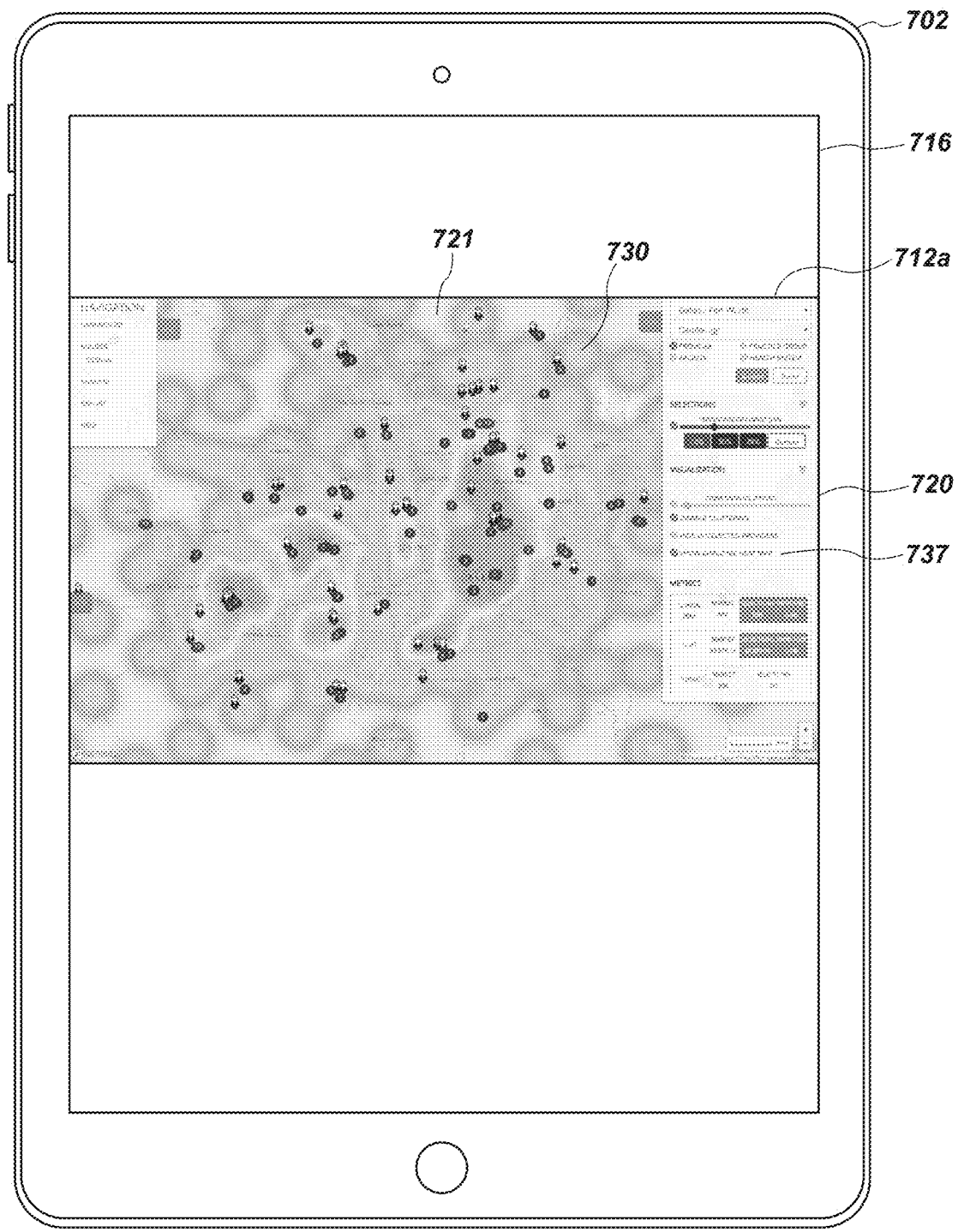

FIG. 7D shows the dashboard GUI 720 with an employee heat map 730 overlaying the map GUI 721 (e.g., when the employee heat map selectable element 737 is selected). In some embodiments, the employee heat map 730 may depict concentrations of employees via a color scale and/or gradient scale. This may enable a user (e.g., network administrator) to view employee locations relative to provider locations and select/improve provider networks based on relative locations of the employees and providers (e.g., keep and/or add providers that are relatively close geographically to employees).

Figure 7E:
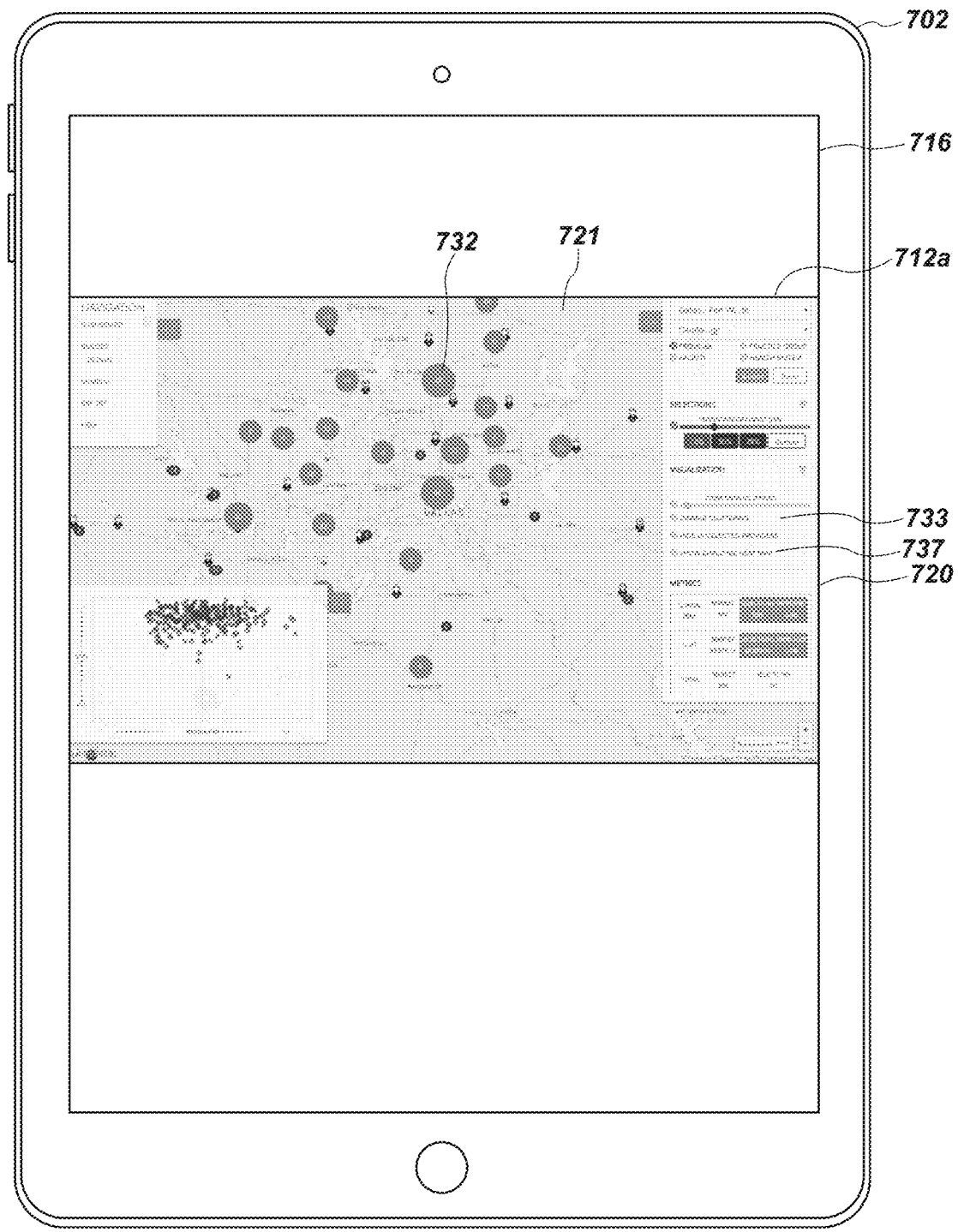

FIG. 7E shows the dashboard GUI 720 with the provider clusters 732 on the map GUI 721 based on the clustering selectable element 733 being unselected. For instance, providers matching the region and specialty may be depicted within clusters instead of being depicted individually. Furthermore, each of the clusters may be depicted as a selectable element that operates in a similar manner to the provider elements 719 discussed above. The foregoing may enable a user (e.g., network administrator) to more quickly recognize concentrations of providers, etc.

Figure 7F:
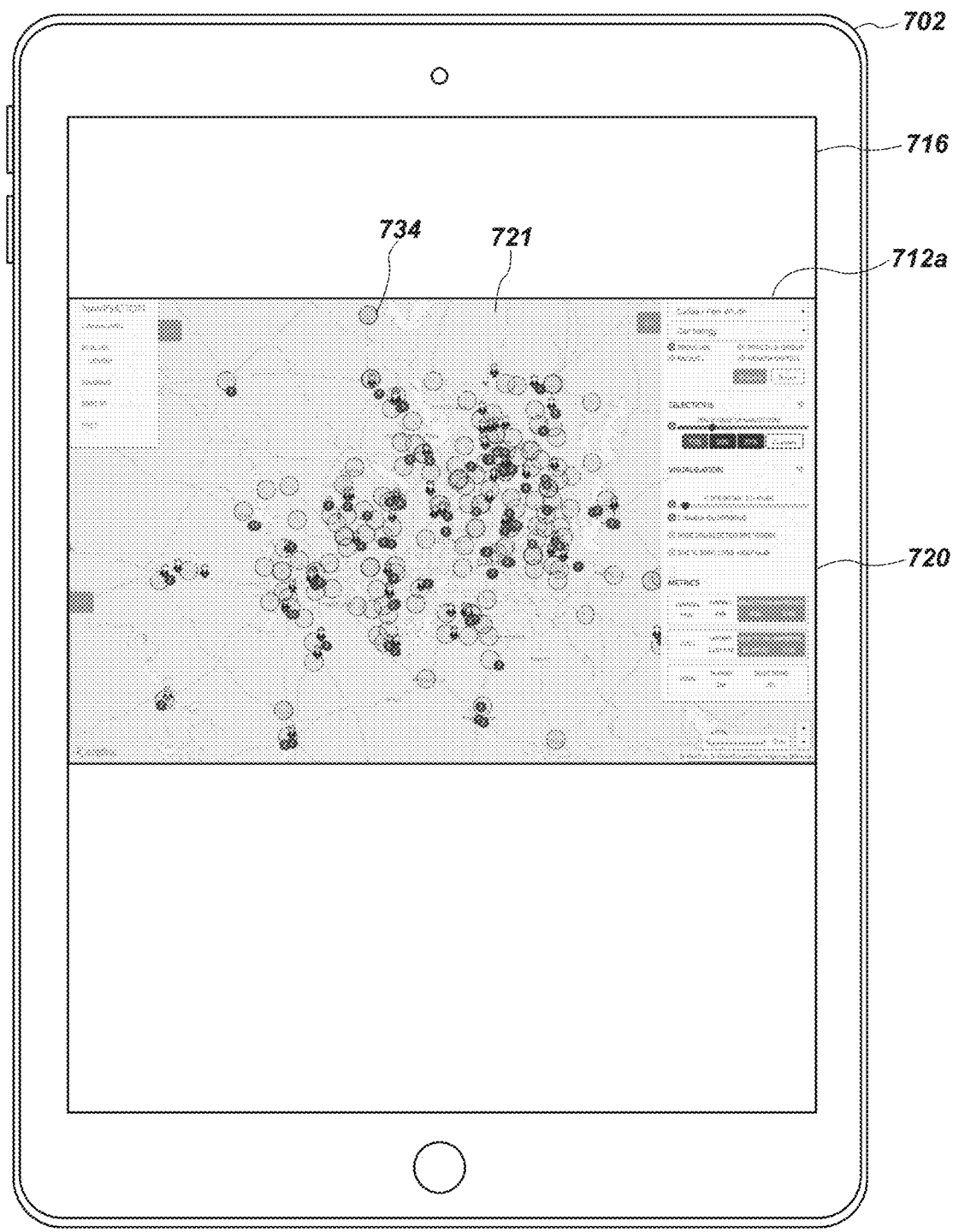

FIG. 7F shows the dashboard GUI 720 with employer locations 734 depicted on the map GUI 721 based on the employer distance selectable element 731 being selected and a particular distance selected. The foregoing may enable a user (e.g., network administrator) to view employer locations relative to provider locations and/or employee locations (e.g., via the employee heat map selectable element 737) and/or only select providers within a particular distance from an employer location.

Figure 7G:
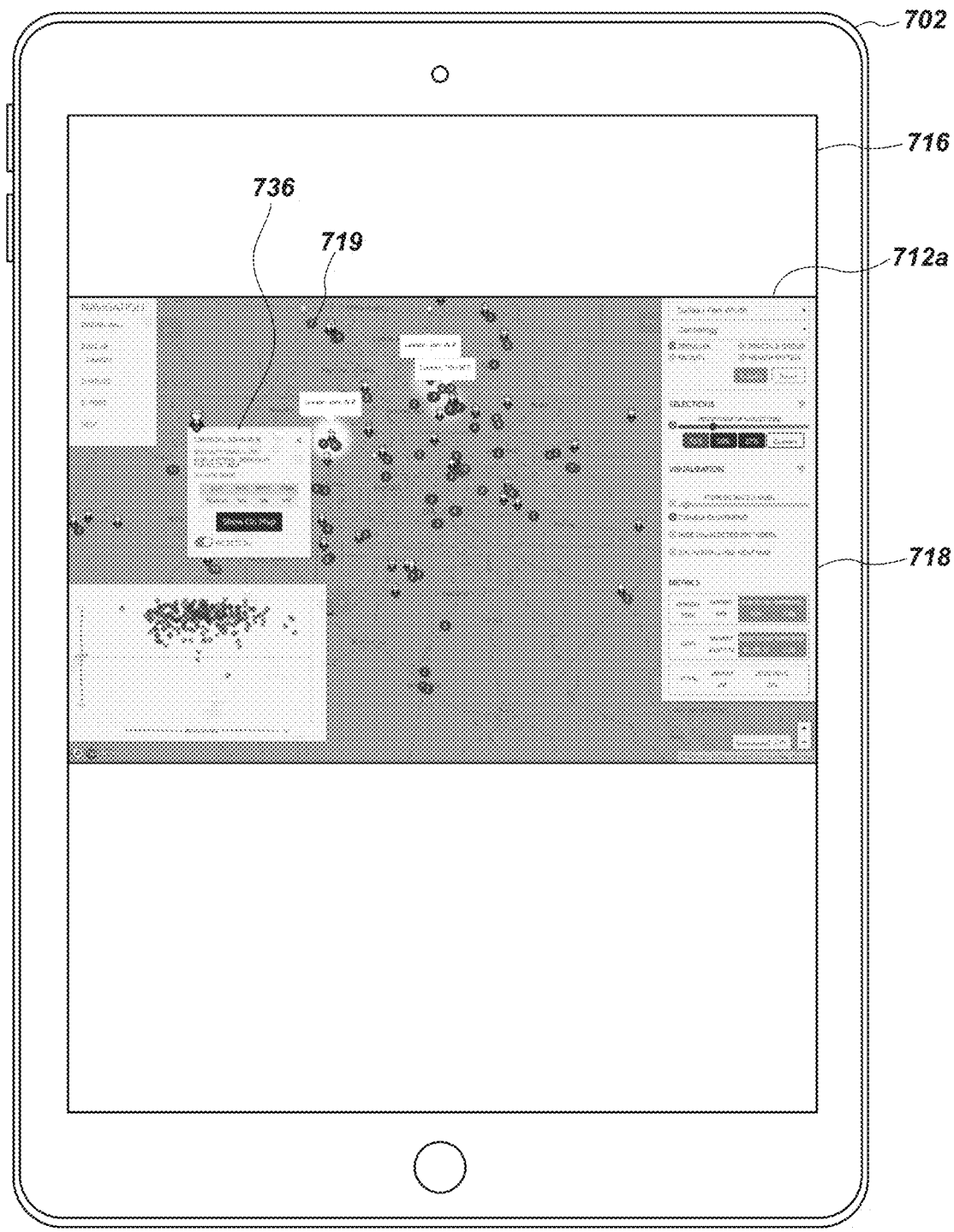

FIG. 7G shows the dashboard GUI 720 with a detail content window 736 regarding a particular provider. For instance, each provider element 719 representing a particular provider may be selectable, such that when the provider element 719 is selected (e.g., clicked on or hovered over), the detail content window 736 will be displayed and which includes the determined composite scores of the associated provider and contact information related to the provider (e.g., address, phone number, website, etc.).

Figure 7H:
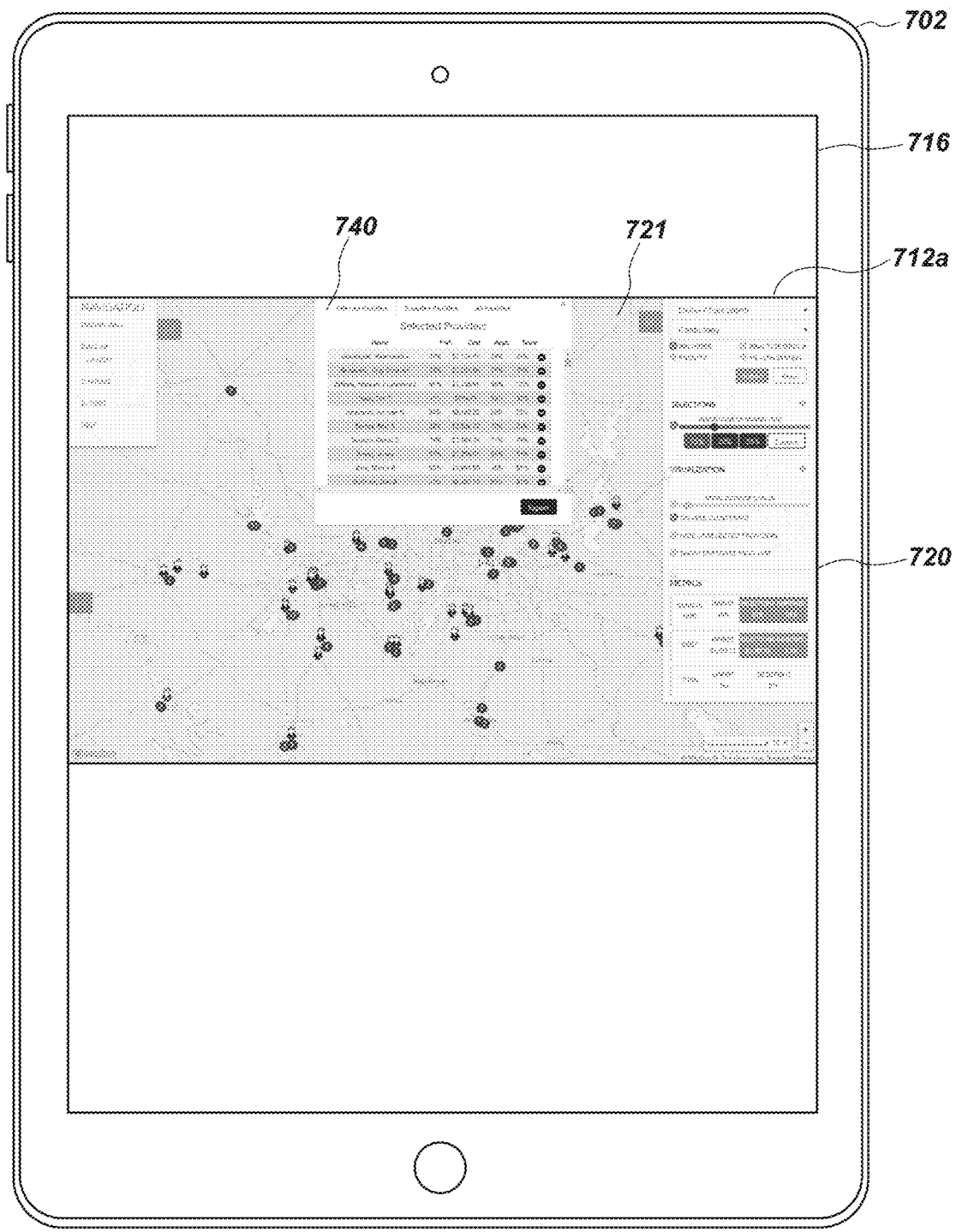

FIG. 7H shows the dashboard GUI 720 with a network generation window 740 for generating (e.g., exporting) a network of providers. For instance, the network generation window 740 may be displayed in response to a selection of an option (e.g., selectable element 729d) to export a network of selected providers. The network generation window 740 may include composite scores for each of the selected providers listed therein. Furthermore, the network generation window 740 may include one or more tabs 742, 744 (not shown) for displaying excluded providers and/or all providers within a given region and specialty. Moreover, the network generation window 740 may include an export selectable element 746 (not shown) for exporting the selected providers as a provider network. For instance, the provider determination system 104 may export the provider network (and the selected providers) as a data file.

Referring to FIGS. 7A-7H together, any number of the selectable elements 731, 733,735, 737 may be selected at a same time. Furthermore, in view of the foregoing, the GUIs and selectable elements depicted in FIGS. 7A-7H may enable a user (e.g., a network administrator) to view performance scores of the selected or excluded providers (or practice groups, facilities, or health systems) within a selected specialty and region compared to a selected benchmark and/or relative to each other. Moreover, one or more of the GUIs depicted in FIGS. 7A-7H may show an effectiveness score, an appropriateness score, and/or a cost score of the providers.

Additionally, the GUIs and selectable elements depicted in FIGS. 7A-7H may enable a user to view an overall performance of a group of providers (or practice groups, facilities, or health systems) within a selected specialty and region relative of all groups of providers within a selected benchmark. Furthermore, one or more of the GUIs may include a curation of the selected and/or excluded providers (or practice groups, facilities, or health systems) within a selected specialty and region curated against the selected benchmark.

Furthermore, the GUIs and selectable elements depicted in FIGS. 7A-7H may enable a user to select a performance score and to view how performance measures (e.g., the performance measures described herein) effected the performance scores of the providers within the selected specialty and region. Moreover, in some embodiments, depending on the performance score that is selected, one or more GUIs may list the performance measures that affect the selected performance score for the providers within the selected specialty and region.

In one or more embodiments, one or more GUIs of the tool application may show areas for improvement for the providers within the selected specialty and region. Furthermore, the areas of improvement may be specific to performance measures.

In some embodiments, the tool application 712a may display potential actions for improving one or more entities (e.g., providers, practice groups, facilities, and/or health systems) within the selected specialty and region that may result in improved performance scores for the entities within the selected specialty and region. For instance, the tool application 712a may depict an anticipated improvement by improving the one or more entities. Accordingly, the tool application 712a may assist administrators of provider networks in identifying areas for improvement within the provider network.

Additionally, in view of the foregoing, a provider assessment system 104 may provider a tool (i.e., tool application 712a) for building a provider network based on performance scores of providers. Additionally, one or more of the GUIs described above may depict overall scores at the specialty and region levels based on the selected specialty and region. Furthermore, a provider assessment system 104 may enable a user to customize a provider network or select a recommended provider network.

Figure 8:
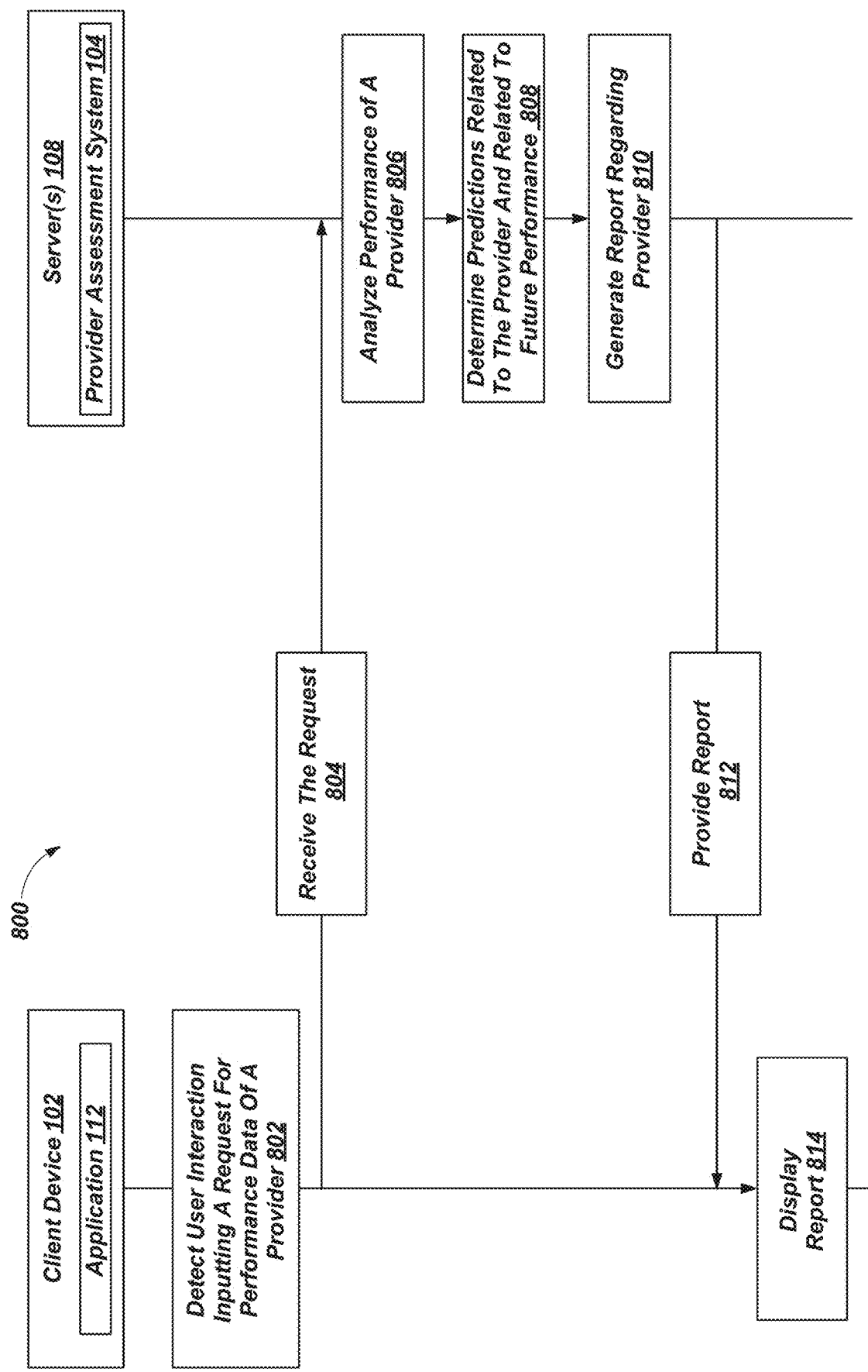
FIG. 8 illustrates a sequence-flow diagram showing various acts of a client device and a provider determination system, in accordance with various embodiments of facilitating communications between client devices and the provider determination system.

FIG. 8 illustrates a sequence-flow diagram 800 showing various acts of a client device 102 and a provider determination system 104, in accordance with various embodiments of facilitating communications between client devices and the provider determination system 104. The client device 102 and the provider determination system 104 shown in FIG. 8 may be example embodiments of the client device 102 and the provider determination system(s) 104 described in regard to FIGS. 1-7H.

As shown in act 802 of FIG. 8, in some embodiments, the application 112 and/or client device 102 detects a user interaction inputting a request for performance data (e.g., scores) of a provider. As used herein, the terms "user interaction" mean a single interaction, or combination of interactions, received from a user by way of one or more input devices (e.g., a touch screen display, a keyboard, a mouse, microphone, camera, etc.) of the client device 102. Furthermore, the user interaction may include one or more of clicking, tapping, or otherwise selecting elements (e.g., letters and/or characters) to include in the message, speaking, and/or capturing video. For example, the application 112 of the client device 102 detects a user interaction inputting a provider name and/or selecting an option to receive provider scores of the provider within the application 112 in response to the prompt. For instance, the detected user interaction may be made via any of the GUIs described above in regard to FIGS. 7A-7H.

In response to the client device 102 detecting a user interaction inputting a request for performance data (e.g., scores) of a provider, a provider assessment system 104 receives the request from the client device 102, as shown in act 804 of FIG. 8. For instance, the provider assessment system 104 may receive a data package including the request for provider performance data. In some embodiments, a provider assessment system 104 may receive a data package via any of the networks described above in regard to FIG. 1.

Upon receiving the request for performance data of a provider, a provider assessment system 104 analyzes a performance of the provider, as shown in act 806 of FIG. 8. Analyzing the performance of the provider may include performing any of the acts described above in regard to FIGS. 2,4, and 7A-7H to determine composites performance scores for the provider. For example, the provider assessment system 104 may analyze claims data via performance measures via any of the manner described herein to determine composite performances scores for the provider at the domain level.

Furthermore, in some embodiments, a provider assessment system 104 determines predictions related to the provider and related to future performance of the provider, as shown in act 808 of FIG. 8. For instance, the provider assessment system 104 may apply any of the prediction models described above in regard to FIG. 4 to measures scores and/or claims data to generate model-predicted measure scores and model-predicted data regarding provider performance.

Additionally, a provider assessment system 104 may generate a report including the determined performance scores of the provider and any predicted behaviors and/or predicted performance scores of the provider, as shown in act 810 of FIG. 8. For instance, the report may include any of the performance scores described above, and the report may include indications on how a provider may act (i.e., behave) in the future.

Upon generating the report, a provider assessment system 104 may provide the report to the client device 102 for display within the application 112 of the client device 102, as shown in act 812 of FIG. 8. A provider assessment system 104 may provide the report to the client device via any of the networks described above in regard to FIG. 1.

In response to receiving the report, the application 112 and/or client device 102 displays the report, as shown in act 814 of FIG. 8. For example, in some embodiments, the application 112 of the client device 102 may display the report within the application 112 within any of the GUIs depicted in FIGS. 7A-7H. Additionally, in one or more embodiments, the application 112 of the client device 102 may display the report as a notification within the application 112. Alternatively, the client device 102 may display the report (e.g., a notification) via the operating system of the client device 102 (e.g., as a push notification).

Referring to acts 802-814 together, a provider assessment system 104 of the present disclosure may enable a user to view performance scores representing past performance, and a provider assessment system 104 of the present disclosure may enable a user to obtain and view data including predictions on how a provider will behave in the future given certain scenarios (e.g., key-clinical decision points).

Figure 9:
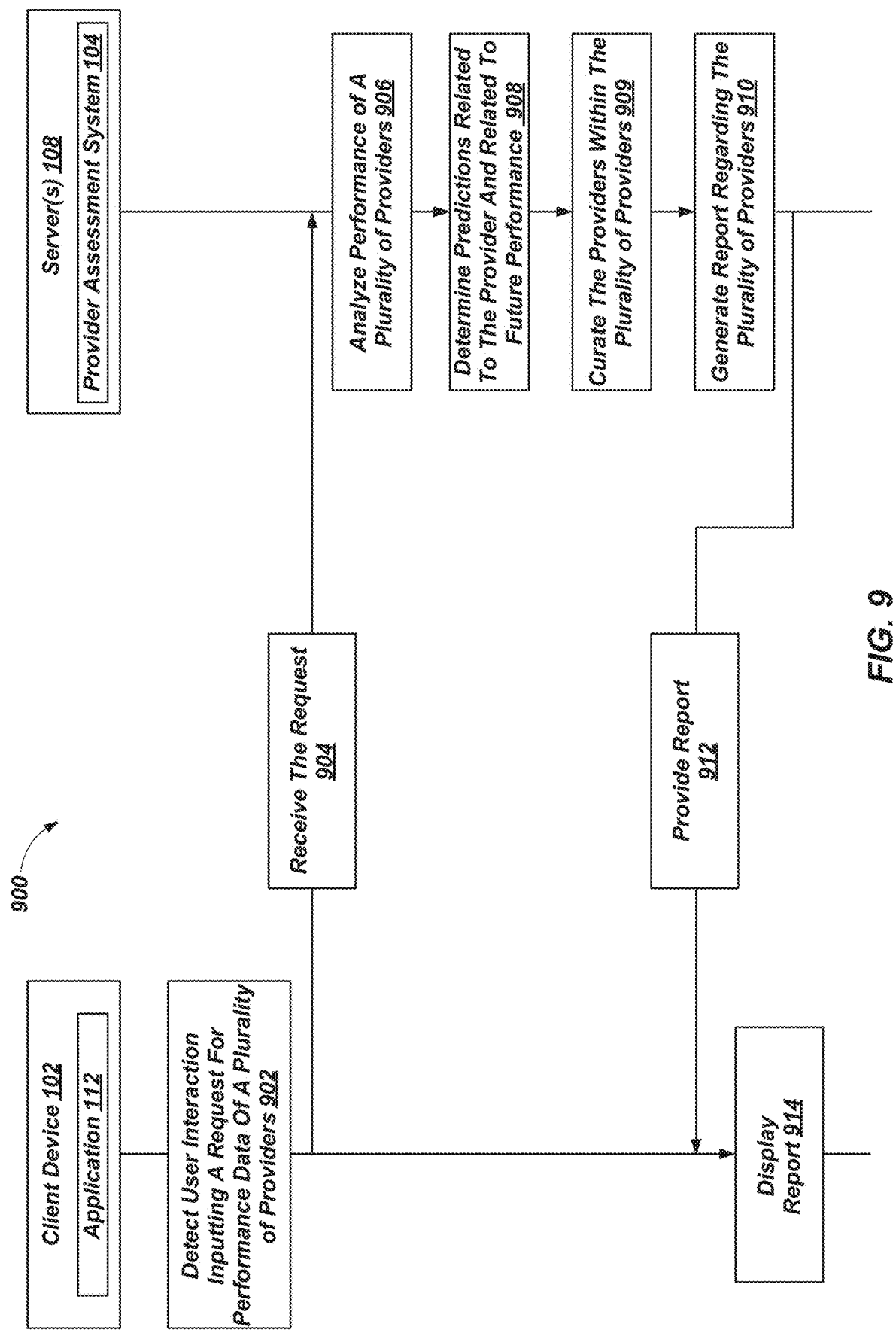
FIG. 9 illustrates a sequence-flow diagram showing various acts of a client device and a provider determination system, in accordance with various embodiments of facilitating communications between client devices and the provider determination system.

FIG. 9 illustrates a sequence-flow diagram 900 showing various acts of a client device 102 and a provider determination system 104, in accordance with various embodiments of facilitating communications between client devices and the provider determination system 104. The client device 102 and the provider determination system 104 shown in FIG. 9 may be example embodiments of the client device 102 and the provider determination system(s) 104 described in regard to FIGS. 1-7H.

As shown in act 902 of FIG. 8, in some embodiments, the application 112 and/or client device 102 detects a user interaction inputting a request for performance data (e.g., scores) of a plurality of providers. The user interaction may include any of the user interactions described above in regard to FIG. 8. Furthermore, the request may include a request for performance data of a plurality of providers within a specific specialty and/or in related to specific condition and/or key-clinical decision.

In response to the client device 102 detecting a user interaction inputting a request for performance data (e.g., scores) of a plurality of providers, a provider assessment system 104 receives the request from the client device 102, as shown in act 904 of FIG. 9. For instance, the provider assessment system 104 may receive a data package including the request for performance data of a plurality of providers. In some embodiments, a provider assessment system 104 may receive the data package via any of the networks described above in regard to FIG. 1.

Upon receiving the request for performance data (e.g., scores) of a plurality of providers, a provider assessment system 104 analyzes a performance of a plurality of providers, as shown in act 906 of FIG. 9. For instance, the provider assessment system 104 may analyze the performance of a plurality of providers within a selected specialty and/or specific to a selected condition and/or key clinical decision point. Analyzing the performance of the plurality of providers may include performing any of the analysis described above in regard to FIGS. 2, 4, and 7A-7H to determine composites performance scores for each of the providers of the plurality of providers.

Furthermore, in some embodiments, a provider assessment system 104 determines predictions related to each provider of the plurality of providers and related to future performance of the each provider of the plurality of providers, as shown in act 908 of FIG. 9. Furthermore, the predictions may be specific to the selected specialty and/or the selected condition and/or key clinical decision. For instance, the provider assessment system 104 may apply any of the prediction models described above in regard to FIG. 4 to measure scores and/or claims data to generate model-predicted measure scores and model-predicted data regarding provider performance of the plurality of providers.

Moreover, upon determining performance scores and/or performance predictions for the plurality of providers, a provider assessment system 104 curates the providers within the plurality of providers, as shown in act 909 of FIG. 9. For instance, a provider assessment system 104 may rank the providers based on the composite performance scores of the providers within the plurality of providers.

Additionally, a provider assessment system 104 may generate a report including the determined performance scores of the plurality of providers and any predicted behaviors and/or predicted performance scores of the plurality of providers, as shown in act 910 of FIG. 9. For instance, the report may include any of the performance scores described above, and the report may include indications on how a provider may act (i.e., behave) in the future. Furthermore, in some embodiments, the report may include the curation of the plurality of providers. For instance, the report may indicate which provider within the plurality of providers will perform the best in the future within the selected specialty and/or in response to the selected condition and/or key clinical decision point.

Upon generating the report, a provider assessment system 104 may provide the report to the client device 102 for display within the application 112 of the client device 102, as shown in act 912 of FIG. 9. A provider assessment system 104 may provide the report to the client device via any of the networks described above in regard to FIG. 1.

In response to receiving the report, the application 112 and/or client device 102 displays the report, as shown in act 914 of FIG. 9. For example, in some embodiments, the application 112 of the client device 102 may display the report within the application 112 within any of the GUIs depicted in FIGS. 7A-7H. Additionally, in one or more embodiments, the application 112 of the client device 102 may display the report as a notification within the application 112. Alternatively, the client device 102 may display the report (e.g., a notification) via the operating system of the client device 102 (e.g., as a push notification).

Referring to acts 902-914 together, a provider assessment system 104 of the present disclosure may enable a user to view performance scores representing past performances of a plurality of providers, and a provider assessment system 104 of the present disclosure may enable a user to obtain and view data including predictions on how the plurality of providers will behave in the future given certain scenarios (e.g., key-clinical decision points). Additionally, a provider assessment system 104 of the present disclosure may enable a user to obtain and view a curation of providers within a plurality of providers. In other words, a provider assessment system 104 of the present disclosure may enable a user to determine which providers within the plurality of providers will perform the best given certain scenarios (e.g., key-clinical decision points) at the domain level.

Figure 10:
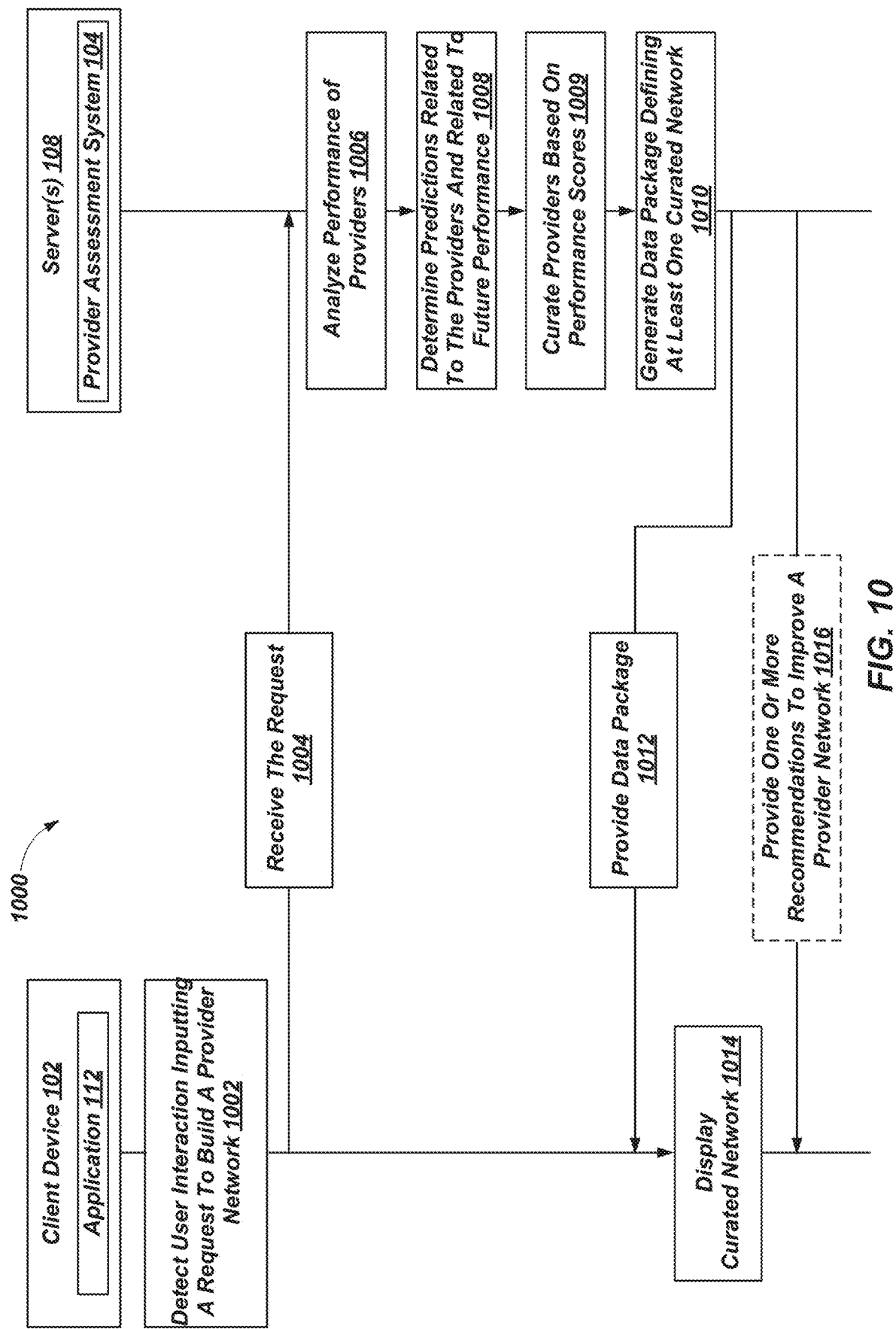
FIG. 10 illustrates a sequence-flow diagram showing various acts of a client device and a provider determination system, in accordance with various embodiments of facilitating communications between client devices and the provider determination system.

FIG. 10 illustrates a sequence-flow diagram 1000 showing various acts of a client device 102 and a provider determination system 104, in accordance with various embodiments of facilitating communications between client devices and the provider determination system 104. The client device 102 and the provider determination system 104 shown in FIG. 10 may be example embodiments of the client device 102 and the provider determination system(s) 104 described in regard to FIGS. 1-7H.

As shown in act 1002 of FIG. 10, in some embodiments, the application 112 and/or client device 102 detects a user interaction inputting a request to build a provider network within a given region and/or across one or more specialties. The user interaction may include any of the user interactions described above in regard to FIG. 8. For instance, the request may be made via interactions with any of the GUIs depicted in FIGS. 7A-7H.

In response to the client device 102 detecting a user interaction inputting a request to build a provider network, a provider assessment system 104 receives the request from the client device, as shown in act 1004 of FIG. 10. For instance, the provider assessment system 104 may receive a data package including the request to build a provider network. In some embodiments, a provider assessment system 104 may receive the data package via any of the networks described above in regard to FIG. 1.

Upon receiving the request to build a provider network, a provider assessment system 104 analyzes the performances of providers within the selected region and/or across the selected specialties, as shown in act 1006 of FIG. 10. For instance, the provider assessment system 104 may analyze the performance of a plurality of providers within a selected region and/or the selected specialties. Analyzing the performance of the plurality of providers may include performing any of the analysis described above in regard to FIGS. 2, 4, and 7A-7H to determine composites performance scores for each of the providers of the plurality of providers.

Furthermore, in some embodiments, a provider assessment system 104 determines predictions related to each provider of the providers within the selected region and/or across the selected specialties and related to future performance of the each provider providers within the selected region and across selected specialties, as shown in act 1008 of FIG. 10. For instance, the provider assessment system 104 may apply any of the prediction models described above in regard to FIG. 4 to generate model-predicted measure scores and model-predicted data regarding provider performance of the providers within the selected region and across selected specialties.

Moreover, upon determining performance scores and/or performance predictions for the providers within the selected region and/or across the selected specialties, a provider assessment system 104 curates the providers within the selected region and across selected specialties, as shown in act 1009 of FIG. 10. For instance, a provider assessment system 104 may rank the providers based on the composite performance scores of the providers within the selected region and/or across the selected specialties.

Additionally, a provider assessment system 104 may generate a data package defining at least one curated network including providers from the selected region and/or across the selected specialties, as shown in act 1010 of FIG. 10. For instance, the at least one curated network may include a certain number (e.g., a list) of the best performing providers, according to the determined performance scores of the providers, within the selected region and/or across the selected specialties. In some embodiments, the provider assessment system 104 may define a plurality of curated networks based the determined performance scores of the providers within the selected region and/or across the selected specialties. For example, the provider assessment system 104 may define a plurality of curated networks, each curated network being specific to a particular specialty, sub-region, conditions, etc. Furthermore, in some embodiments, provider assessment system 104 may define a plurality of curated networks curated by differing performances scores. For example, a first curated network may be curated based on appropriateness scores, a second curated network may be curated based on effectiveness scores, and a third curated network may be curated based on cost scores.

Upon defining the at least one curated network, a provider assessment system 104 may provide the data package defining the at least one curated network to the client device 102 for displaying data (e.g., the list) regarding the at least one curated network within the application 112 of the client device 102, as shown in act 1012 of FIG. 10. A provider assessment system 104 may provide the data package to the client device 102 via any of the networks described above in regard to FIG. 1.

In response to receiving the data package, the application 112 and/or client device 102 displays the at least one curated network, as shown in act 1014 of FIG. 10. For example, in some embodiments, the application 112 of the client device 102 may display a list of the providers within the at least one curated network, and the performance scores associated with each provider within the list within the application 112 within any of the GUIs depicted in FIGS. 7A-7H. Additionally, in one or more embodiments, the application 112 of the client device 102 may display the at least one curated network as a notification within the application 112. Alternatively, the client device 102 may display the at least one curated network (e.g., a notification) via the operating system of the client device 102 (e.g., as a push notification).

Referring to acts 1002-1014 together, a provider assessment system 104 of the present disclosure may enable a user to build at least one network based on performance scores of the providers within a selected region and/or selected specialties. Additionally, as is described above in regard to FIGS. 7A-7H, a provider assessment system 104 of the present disclosure may enable a user to modify and change a built provider network based on performance scores of providers within the provider network.

In some embodiments, a provider assessment system 104 may provide one or more recommendations to improve a provider network based on the determined performance scores of the provider within a built network, as shown in act 1016 of FIG. 10. For instance, a provider assessment system 104 may provide recommendations according to any of the manners described above in regard to and depicted in FIGS. 7A-7H. As a few non-limiting examples, a provider assessment system 104 may recommend exchanging a relatively poor performing provider with a better performing provider that is within a selected region and specialty, expand the selected region to include relatively high performing providers, contract the selected region to remove low performing providers, etc.

Figure 11:
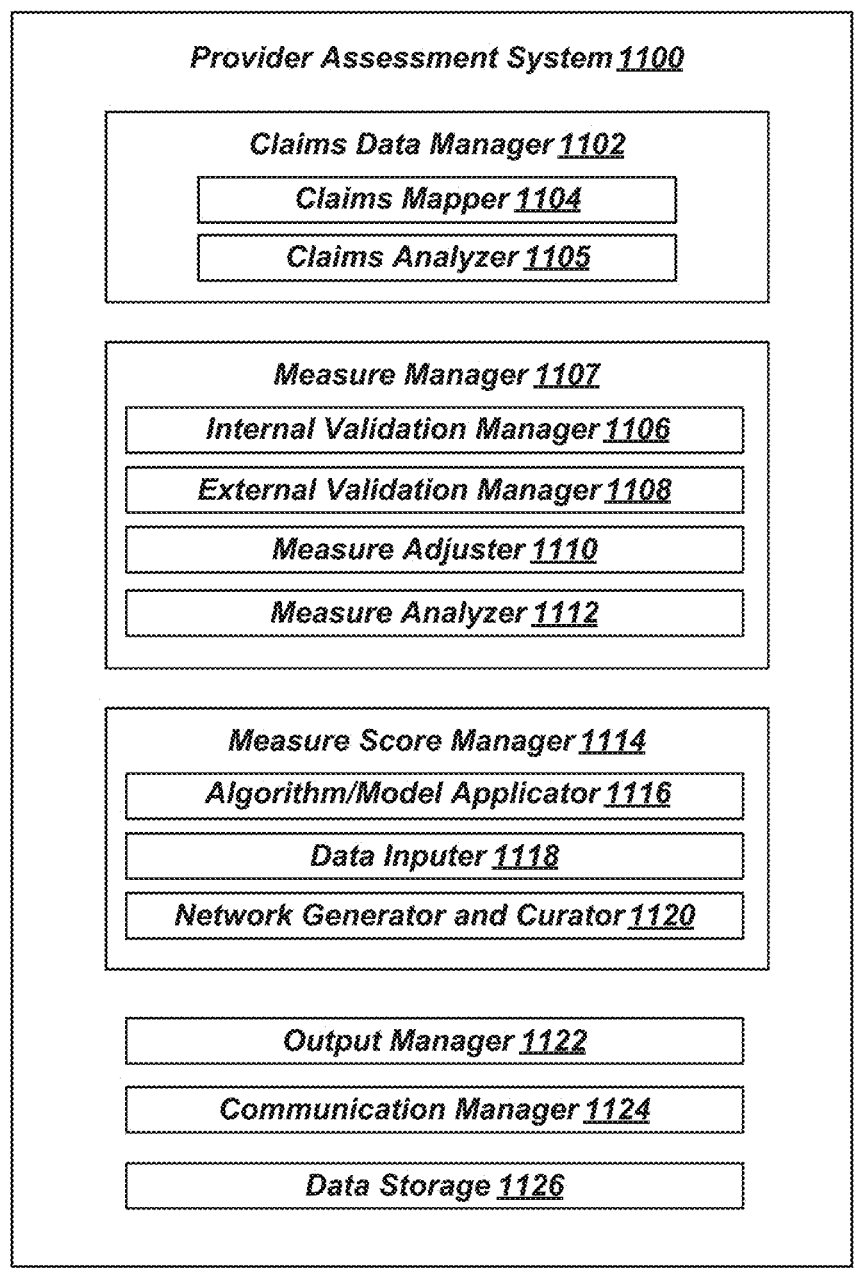
FIG. 11 illustrates a detailed schematic diagram of a provider assessment system according to one or more embodiments of the present disclosure.

FIG. 11 illustrates a detailed schematic diagram of a provider assessment system 1100 according to one or more embodiments of the present disclosure.

The provider assessment system 1100 can be implemented using a computing device including at least one processor executing instructions that cause the provider assessment system 1100 to perform the processes described herein. In some embodiments, the provider assessment system 1100 can all be implemented by a single server device, or across multiple server devices. Additionally or alternatively, a combination of one or more server devices and one or more client devices can implement the provider assessment system 1100. Furthermore, in one embodiment, provider assessment system 1100 can comprise hardware, such as a special-purpose processing device to perform a certain function. Additionally or alternatively, the provider assessment system 1100 can comprise a combination of computer-executable instructions and hardware.

In some embodiments, the provider assessment system 1100 may include a claims data manager 1102. The claims data manager 1102 may manage claims data received from a third-party system. Furthermore, the claims data manager 1102 may provide the claims data to other elements of the provider assessment system 1100. In one or more embodiments, the claims data manager 1102 may include a claims mapper 1104 and a claims analyzer 1105. In some embodiments, the claims mapper 1104 may map clinical priority areas and candidate measures to claims data via any of the manners described above in regard to acts 204, 206, and 208 of FIG. 2. Furthermore, the claims analyzer may analyze claims data via any of the manners described in regard to act 202 of FIG. 2.

In one or more embodiments, the provider assessment system 1100 may further include a measure manager 1107 that includes an internal validation manager 1106, an external validation manager 1108, a measure adjuster 1110, and a measure analyzer 1112. In some embodiments, the internal validation manager 1106 may validate defined measures via any of the manners described above in regard to act 210 of FIG. 2. The external validation manager 1108 may validate defined measures via any of the manners described above in regard to acts 212 and 216 of FIG. 2. Additionally, the measure adjuster 1110 may adjust specifications of measures according to any of the manners described above in regard to acts 208 and 214 of FIG. 2. Moreover, the measure analyzer 1112 may map statistical performance of a measures and may determine statistical relationships across measures according to any of the manners described above in regard to act 218 of FIG. 2 and act 402 of FIG. 4.

In some embodiments, the provider assessment system 1100 may also include a measure score manager 1114 that includes an algorithm/model applicator 1116, a data imputer 1118, and a network generator and curator 1120. In one or more embodiments, the algorithm/model applicator 116 may apply statistical models, predictive models, principal components analysis, and/or machine learning models to determined measure scores and/or data via any of the manners described above in regard to acts 404, 408, and/or 410 of FIG. 4. Additionally, in some embodiments, the data imputer 1118 may impute data via any of the manners described above in regard to act 406 of FIG. 4. Likewise, the network generator and curator 1120 may generate networks and may curate networks via any of the manners described above in regard to act 412 of FIG. 4 and FIGS. 9 and 10.

Furthermore, the provider assessment system 1100 may include an output manager 1122 and a communication manager 1124. In some embodiments, the output manager 1122 may output reports, performance scores, curated networks, built networks, etc., to an application (e.g., tool) of the provider assessment system 1100 via any of the manners described above in regard to act 414 of FIG. 4 and FIGS. 8-10. Moreover, the communication manager 1124 may enable and may manage communication between the provider assessment system 1100, third-party systems, and client devices via any of the manners described herein.

The provider assessment system 1100 may also include a data storage 1126 (i.e., database) in which the provider assessment system 1100 may store measure data, provider data, performance scores, network definitions, region data, etc.

Figure 12:
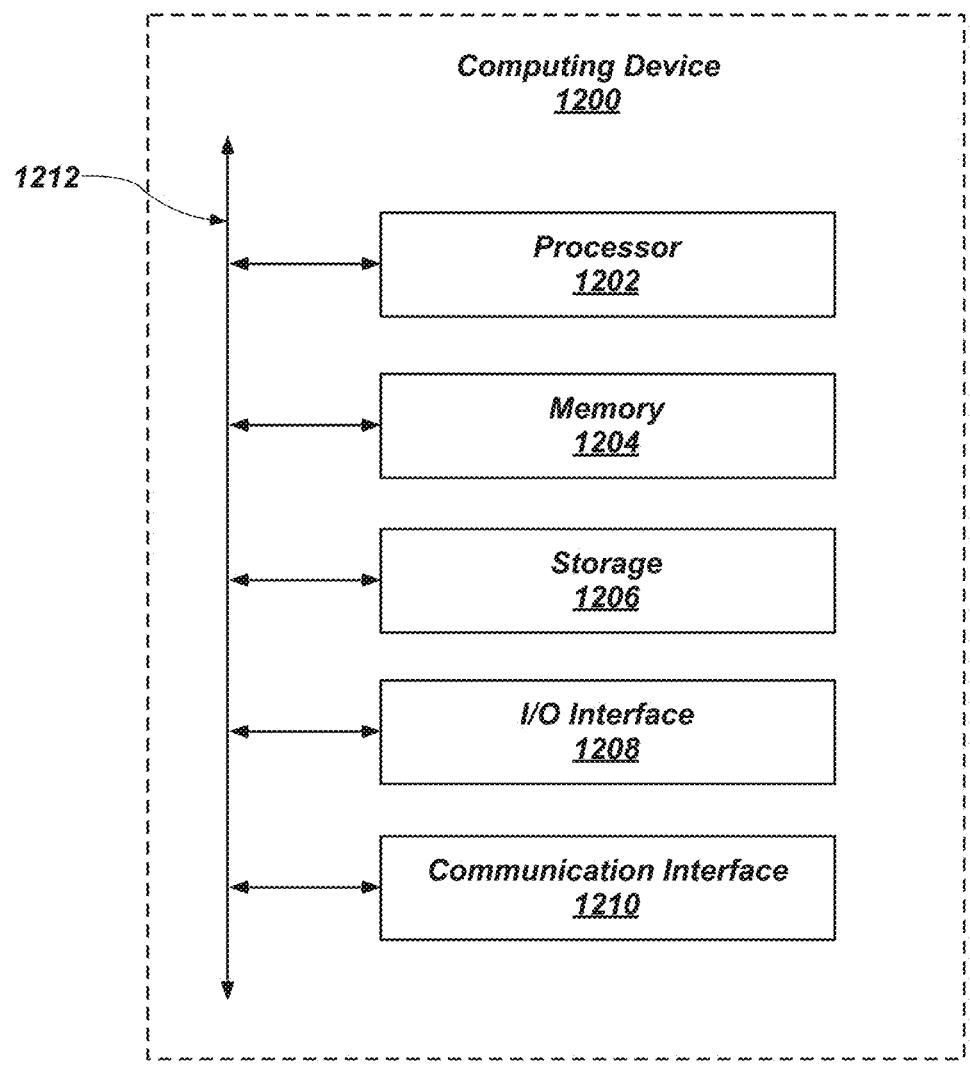
FIG. 12 illustrates a block diagram of an exemplary computing device in accordance with one or more embodiments.

FIG. 12 is a block diagram of an exemplary computing device 1200 that may be utilized as a client device (e.g., client device 102) and/or a provider assessment system (e.g., provider assessment system 104) that may be configured to perform one or more of the processes described above. One will appreciate that one or more computing devices may implement the computing device 1200. The computing device 1200 can comprise a processor 1202, a memory 1204, a storage device 1206, an I/O interface 1208, and a communication interface 1210, which may be communicatively coupled by way of a communication infrastructure 1212. While an exemplary computing device is shown in FIG. 12, the components illustrated in FIG. 12 are not intended to be limiting. Additional or alternative components may be used in other embodiments. Furthermore, in certain embodiments, the computing device 1200 can include fewer components than those shown in FIG. 12. Components of the computing device 1200 shown in FIG. 12 will now be described in additional detail.

In one or more embodiments, the processor 1202 includes hardware for executing instructions, such as those making up a computer program. As an example and not by way of limitation, to execute instructions, the processor 1202 may retrieve (or fetch) the instructions from an internal register, an internal cache, the memory 1204, or the storage device 1206 and decode and execute them. In one or more embodiments, the processor 1202 may include one or more internal caches for data, instructions, or addresses. As an example and not by way of limitation, the processor 1202 may include one or more instruction caches, one or more data caches, and one or more translation lookaside buffers (TLBs). Instructions in the instruction caches may be copies of instructions in the memory 1204 or the storage device 1206.

The memory 1204 may be used for storing data, metadata, and programs for execution by the processor(s). The memory 1204 may include one or more of volatile and non-volatile memories, such as Random Access Memory ("RAM"), Read-Only Memory ("ROM"), a solid state disk ("SSD"), Flash memory, Phase Change Memory ("PCM"), or other types of data storage. The memory 1204 may be internal or distributed memory.

The storage device 1206 includes storage for storing data or instructions. As an example and not by way of limitation, storage device 1206 can comprise a non-transitory storage medium described above. The storage device 1206 may include a hard disk drive (HDD), a floppy disk drive, flash memory, an optical disc, a magneto-optical disc, magnetic tape, or a Universal Serial Bus (USB) drive or a combination of two or more of these. The storage device 1206 may include removable or non-removable (or fixed) media, where appropriate. The storage device 1206 may be internal or external to the computing device 1200. In one or more embodiments, the storage device 1206 is non-volatile, solid-state memory. In other embodiments, the storage device 1206 includes read-only memory (ROM). Where appropriate, this ROM may be mask programmed ROM, programmable ROM (PROM), erasable PROM (EPROM), electrically erasable PROM (EEPROM), electrically alterable ROM (EAROM), or flash memory or a combination of two or more of these.

The I/O interface 1208 allows a user to provide input to, receive output from, and otherwise transfer data to and receive data from computing device 1200. The I/O interface 1208 may include a mouse, a keypad or a keyboard, a touch screen, a camera, an optical scanner, network interface, modem, other known I/O devices or a combination of such I/O interfaces. The I/O interface 1208 may include one or more devices for presenting output to a user, including, but not limited to, a graphics engine, a display (e.g., a display screen), one or more output drivers (e.g., display drivers), one or more audio speakers, and one or more audio drivers. In certain embodiments, the I/O interface 1208 is configured to provide graphical data to a display for presentation to a user. The graphical data may be representative of one or more graphical user interfaces and/or any other graphical content as may serve a particular implementation.

The communication interface 1210 can include hardware, software, or both. In any event, the communication interface 1210 can provide one or more interfaces for communication (such as, for example, packet-based communication) between the computing device 1200 and one or more other computing devices or networks. As an example and not by way of limitation, the communication interface 1210 may include a network interface controller (NIC) or network adapter for communicating with an Ethernet or other wire-based network or a wireless MC (WNIC) or wireless adapter for communicating with a wireless network, such as a WI-FI.

Additionally or alternatively, the communication interface 1210 may facilitate communications with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, the communication interface 1210 may facilitate communications with a wireless PAN (WPAN) (such as, for example, a BLUETOOTH®WPAN), a WI-FI network, a WI-MAX network, a cellular telephone network (such as, for example, a Global System for Mobile Communications (GSM) network), or other suitable wireless network or a combination thereof.

Additionally, the communication interface 1210 may facilitate communications various communication protocols. Examples of communication protocols that may be used include, but are not limited to, data transmission media, communications devices, Transmission Control Protocol ("TCP"), Internet Protocol ("IP"), File Transfer Protocol ("FTP"), Telnet, Hypertext Transfer Protocol ("HTTP"), Hypertext Transfer Protocol Secure ("HTTPS"), Session Initiation Protocol ("SIP"), Simple Object Access Protocol ("SOAP"), Extensible Mark-up Language ("XML") and variations thereof, Simple Mail Transfer Protocol ("SMTP"), Real-Time Transport Protocol ("RTP"), User Datagram Protocol ("UDP"), Global System for Mobile Communications ("GSM") technologies, Code Division Multiple Access ("CDMA") technologies, Time Division Multiple Access ("TDMA") technologies, Short Message Service ("SMS"), Multimedia Message Service ("MMS"), radio frequency ("RF") signaling technologies, Long Term Evolution ("LTE") technologies, wireless communication technologies, in-band and out-of-band signaling technologies, and other suitable communications networks and technologies.

The communication infrastructure 1212 may include hardware, software, or both that couples components of the computing device 1200 to each other. As an example and not by way of limitation, the communication infrastructure 1212 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination thereof.

The embodiments of the disclosure described above and illustrated in the accompanying drawing figures do not limit the scope of the invention, since these embodiments are merely examples of embodiments of the invention, which is defined by the appended claims and their legal equivalents. Any equivalent embodiments are intended to be within the scope of this invention. Indeed, various modifications of the present disclosure, in addition to those shown and described herein, such as alternative useful combinations of the content features described, may become apparent to those skilled in the art from the description. Such modifications and embodiments are also intended to fall within the scope of the appended claims and legal equivalents.

I claim:

1. A computer-implemented method of generating a performance measure, comprising:
    first mapping at least one clinical priority area and at least one candidate measure concept to one or more coding fields of claims data;
    wherein the at least one candidate measure concept is identified based, at least in part, on an identified key-clinical decision point, the key-clinical decision point based, at least in part, on a decision represented in the claims data and made by a provider before an initial diagnosis of a condition of the patient;
    defining at least one first performance measure based on the one or more coding fields of claims data mapped to the at least one clinical priority area and the at least one candidate measure concept;
    performing one or more validation processes using the at least one first performance measure;
    obtaining a validation result responsive to the one or more validation processes;
    adjusting one or more specifications of the at least one first performance measure based on the obtained validation result;
    second mapping the at least one clinical priority area and the at least one candidate measure concept to one or more coding fields of claims data responsive to the validation result; and
    obtaining at least one final performance measure responsive to the second mapping;
    provide, to a user via a graphical user interface (GUI) of a client device, one or more performance measures based, at least in part, on the at least one final performance measure responsive to a user request for performance data.

2. The method of claim 1, further comprising obtaining at least one final performance measure responsive the second mapping.

3. The method of claim 1, wherein first mapping at least one clinical priority area and at least one candidate measure concept to one or more coding fields of claims data comprises first mapping at least one clinical priority area and at least one candidate measure concept to coding fields of claims data via one or more of field mapping or field value mapping methodologies.

4. The method of claim 1, further comprising obtaining the at least one clinical priority area, wherein the at least one clinical priority area comprises one or more of low-risk obstetrics, orthopedic joint surgery, orthopedic spinal surgery, cardiology, primary care, gastroenterology, or pulmonology.

5. The method of claim 1, further comprising obtaining the at least one candidate measure concept, wherein the at least one candidate measure concept comprises an existing measure from existing measure inventories of a provider assessment system.

6. The method of claim 5, wherein obtaining the at least one candidate measure concept comprises:
    analyzing claims data to identify a plurality of patients' journeys indicated in the claims data within a given clinical area;
    identifying areas within the plurality of patients' journeys where measurable variation occurs between journeys of different patients; and
    identifying the measurable areas of variation as the at least one candidate measure concept.

7. The method of claim 1, further comprising, upon defining the at least one first performance measure based on the one or more coding fields of the claims data mapped to at least one clinical priority area and at least one candidate measure concept, refining specifications of the at least one first performance measure based on a patient population, numerators, and denominators reflected in the claims data.

8. The method of claim 1, wherein performing one or more validation processes comprises performing an external validation process by:
    providing specifications of the first performance measure to a third-party system; and
    receiving feedback data from the third-party system regarding the specifications of the initial performance measure.

9. The method of claim 8, upon receiving the feedback data, second mapping the first performance measure to one or more coding fields of claims data based on the feedback data.

10. The method of claim 1, wherein performing one or more validation processes comprises performing an internal validation process.

11. The method of claim 1, further comprising determining at least one performance score of a provider utilizing the at least one final performance measure.

12. The method of claim 11, wherein determining at least one performance score of a provider comprises:
    receiving, from a third-party system, claims data;
    applying the at least one final performance measure to the claims data to determine measure scores of the provider, the measure scores being related to key-clinical decision points within condition-based patient journeys represented in the claims data;
    outputting one or more data packages representing the determined measure scores;
    applying a principal components analysis to the one or more data packages to determine composite performance scores of the provider based on the determined measure scores; and
    generating a performance data package including the determined composite performance scores.

13. A system comprising:
    at least one processor; and
    at least one non-transitory computer-readable storage medium storing instructions thereon that, when executed by the at least one processor, cause the system to:
    upon obtaining at least one clinical priority area and at least one candidate measure concept, first map the at least one clinical priority area and the at least one candidate measure concept to one or more coding fields of claims data;
    wherein the at least one candidate measure concept is identified based, at least in part, on an identified key-clinical decision point, the key-clinical decision point based, at least in part, on a decision represented in the claims data and made by a provider before an initial diagnosis of a condition of the patient;
    define at least one first performance measure based on the one or more mapped coding fields of claims data;
    validate the at least one first performance measure via at least one validation process;

adjusting one or more specifications of the at least one first performance measure based, at least in part, on a validation result obtained responsive to the at least one validation process;

second map the at least one clinical priority area and the at least one candidate measure concept to one or more coding fields of claims data based on the obtained validation result; and obtaining at least one final performance measure responsive to the second mapping provide, to a user via a graphical user interface (GUI) of a client device, one or more performance measures based, at least in part, on the at least one final performance measure responsive to a user request for performance data.

14. The system of claim 13, further comprising instructions that, when executed by the at least one processor, cause the system to: store the at least one final performance measure within a library of performance measures within a database.

15. The system of claim 13, wherein first mapping the at least one clinical priority area and the at least one candidate measure concept to one or more coding fields of claims data comprises first mapping via one or more of field mapping or field value mapping methodologies.

16. The system of claim 13, further comprising instructions that, when executed by the at least one processor, cause the system to: determine at least one performance score of a provider utilizing the at least one final performance measure.

17. The system of claim 13, wherein the at least one validation process comprises one or more of an internal validation process and an external validation process.

18. The system of claim 16, wherein determining at least one performance score of a provider comprises:

receiving, from a third-party system, claims data;

applying the at least one final performance measure to the claims data to determine measure scores of the provider, the measure scores being related to key-clinical decision points within condition-based patient journeys represented in the claims data;

outputting one or more data packages representing the determined measure scores;

applying a principal components analysis to the one or more data packages to determine composite performance scores of the provider based on the determined measure scores; and generating a performance data package including the determined composite performance scores.

19. A computer-implemented method of determining a performance score of a provider, comprising:

first mapping at least one clinical priority area and at least one candidate measure concept to one or more coding fields of claims data;

wherein the at least one candidate measure concept is identified based, at least in part, on an identified key-clinical decision point, the key-clinical decision point based, at least in part, on a decision represented in the claims data and made by a provider before an initial diagnosis of a condition of the patient;

defining at least one first performance measure based on the one or more coding fields of claims data mapped to the at least one clinical priority area and the at least one candidate measure concept;

performing one or more validation processes using the at least one first performance measure;

obtaining a validation result responsive to the one or more validation processes;

adjusting one or more specifications of the at least one first performance measure based on the obtained validation result;

second mapping the at least one clinical priority area and the at least one candidate measure concept to one or more coding fields of claims data responsive to the validation result;

obtaining at least one final performance measure responsive to the second mapping;

obtaining, from a third-party, claims data include data specific to the provider; and applying the at least one final performance measure to the claims data to determine at least one composite performance score of the provider;

provide, to a user via a graphical user interface (GUI) of a client device, the at least one composite performance score responsive to a user request for performance data.

20. The method of claim 19, wherein performing the first mapping comprises performing in first mapping process, and wherein performing the second mapping comprises performing the first mapping process.

21. The method of claim 19, wherein performing the first mapping comprises performing in first mapping process, and wherein performing the second mapping comprises performing a second, different mapping process.

* * * * *